US008277811B2

(12) United States Patent
Zeng

(10) Patent No.: US 8,277,811 B2
(45) Date of Patent: Oct. 2, 2012

(54) COMPOSITIONS AND METHODS FOR INDUCING CHIMERISM IN A SUBJECT

(75) Inventor: Defu Zeng, Arcadia, CA (US)

(73) Assignee: City of Hope, Duarte, CA (US)

( * ) Notice: Subject to any disclaimer, the term of this patent is extended or adjusted under 35 U.S.C. 154(b) by 524 days.

(21) Appl. No.: 11/699,641

(22) Filed: Jan. 29, 2007

(65) Prior Publication Data

US 2007/0207129 A1 Sep. 6, 2007

Related U.S. Application Data

(62) Division of application No. 11/226,867, filed on Sep. 13, 2005, now abandoned.

(60) Provisional application No. 60/609,850, filed on Sep. 13, 2004.

(51) Int. Cl.
*A61K 39/395* (2006.01)
(52) U.S. Cl. .................. 424/154.1; 424/93.7; 424/144.1
(58) Field of Classification Search .................. None
See application file for complete search history.

(56) References Cited

U.S. PATENT DOCUMENTS

| 5,583,002 | A * | 12/1996 | Ochoa et al. ................. 435/7.23 |
| 5,762,927 | A * | 6/1998 | Knechtle et al. ............ 424/93.7 |
| 5,767,072 | A * | 6/1998 | Vitetta et al. ..................... 514/12 |
| 7,186,697 | B2 * | 3/2007 | Marasco et al. ............ 514/44 R |
| 2002/0182727 | A1 * | 12/2002 | Freeman et al. .............. 435/325 |
| 2005/0238626 | A1 | 10/2005 | Yang et al. |
| 2010/0249039 | A1 * | 9/2010 | Zangemeister-Wittke et al. ............................ 514/19.3 |

OTHER PUBLICATIONS

Baker et al, Expansion of cytolytic CD8+ natural killer T cells with limited capacity for graft-versus-host disease induction due to interferon g production, Blood, 2001, pp. 2922-2932.*
Annunziato, F., et al. 1999. Assessment of chemokine receptor expression by human Th1 and Th2 cells in vitro and in vivo. J Leukoc Biol 65:691-699.
Atkinson, M.A., Leiter, E.H. 1999. The NOD mouse model of type 1 diabetes: As good as it gets? Nat Med 5:601-604.
Beilhack, G.F., et al. 2003. Purified allogeneic hematopoietic stem cell transplantation blocks diabetes pathogenesis in NOD mice. Diabetes 52:59-68.
Belghith, M., et al. 2003. TGF-beta-dependent mechanisms mediate restoration of self-tolerance induced by antibodies to CD3 in overt autoimmune diabetes. Nat Med 9:1202-1208.
Blazer, B.R., Taylor, P.A., Vallera, D.A. 1994. In vivo or in vitro anti-CD3 epsilon chain monoclonal antibody therapy for the prevention of lethal murine graft-versus-host disease across the major histocompatibility barrier in mice[1]. J Immunol 152:3665-3674.
Blazar, B.R., et al. 1997. Anti-CD3 epsilon F(ab')$_2$ fragments inhibit T cell expansion in vivo during graft-versus-host disease or the primary immune response to nominal antigen[1,2]. J Immunol 159:5821-5833.
Bluestone, J.A., Abbas, A.K. 2003. Natural versus adaptive regulatory T cells. Nat Rev Immunol 3:253-257.
Burt, R.K., Traynor, A. 1998. Hematopoietic stem cell therapy of autoimmune diseases. Curr Opin Hematol 5:472-477.
Campbell, D.J., et al. 2003. Targeting T cell responses by selective chemokine receptor expression. Semin Immunol 15:277-286.
Castano, L., Eisenbarth, G.S. 1990. Type-I diabetes: a chronic autoimmune disease of human, mouse, and rat. Annu Rev Immunol 8:647-679.
Chatenoud, L., Primo, J., Bach, J.F. 1997. CD3 antibody-induced dominant self tolerance in overtly diabetic NOD mice[1]. J Immunol 158:2947-2954.
Cooke, K.R., Ferrara, J.L. 2003. A protective gene for graft-versus-host disease. N Engl J Med 349:2183-2184.
Dor, Y., Brown, J., Martin, O., Melton, D.A. 2004. Adult pancreatic beta-cells are formed by self-duplication rather than stem-cell differentiation. Nature 429:41-46.
Exner, B.G., Groninger, J.H., Ildstad, S.T. 1997. Bone marrow transplantation for therapy in autoimmune disease. Stem Cells 15(suppl 1):171-175.
Ferrara, J.L. 2000. Pathogenesis of acute graft-versus-host disease: cytokines and cellular effectors. J Hematother Stem Cell Res 9:299-306.
Ferrara, J., Antin, J. 2004. The pathophysiology of Graft-vs-Host Disease. Hematopoietic Cell Transplantation. Malden: Blackwell Science Ltd. 353-368.
Gandy, K.L., Domen, J., Aguila, H., Weissman, I.L. 1999. CD8$^{30}$ TCR$^+$ and CD8$^+$TCR$^-$ cells in whole bone marrow facilitate the engraftment of hematopoietic stem cells across allogeneic barriers. Immunity 11:579-590. Gonzalez, M., et al. 2002. The balance between donor T cell anergy and suppression versus lethal graft-versus-host disease is determined by host conditioning[1]. J Immunol 169:5581-5589.
Goudy, K.S., et al. 2003. Systemic overexpression of IL-10 induces CD4$^+$CD25$^+$ cell populations in vivo and ameliorates type 1 diabetes in nonobese diabetic mice in a dose-dependent fashion[1]. J Immunol 171:2270-2278.

(Continued)

*Primary Examiner* — Maria Marvich
(74) *Attorney, Agent, or Firm* — Perkins Coie LLP; Patrick Morris

(57) ABSTRACT

Prevention of autoimmune disease and induction of transplantation tolerance in a recipient can be achieved by induction of mixed chimerism via bone marrow transplantation (BMT), but this procedure requires total body irradiation (TBI)-conditioning of the recipient. The toxicity of radiation and potential for graft versus host disease (GVHD) prevents its clinical application. Donor CD8$^+$ T cells play a critical role in facilitation of engraftment, but also contribute to induction of GVHD in TBI-conditioned recipients. It is disclosed herein that high doses of donor CD8$^+$ T cells in combination with donor bone marrow (BM) cells induces mixed chimerism without GVHD in recipients conditioned with anti-CD3 mAb. These chimeric recipients display donor specific tolerance and reversal of insulitis. These results establish that donor CD8$^+$ T cell-mediated facilitation of engraftment can be separated from GVHD in non-irradiated recipients. This regimen has application in the treatment of autoimmune disorders and the induction of transplantation tolerance.

2 Claims, 6 Drawing Sheets

OTHER PUBLICATIONS

Hancock, W.W., et al. 2000. Requirement of the chemokine receptor CXCR3 for acute allograft rejection. J Exp Med 192:1515-1519.
Hancock, W.W., et al. 2001. Donor-derived IP-10 initiates development of acute allograft rejection. J Exp Med 193:975-980.
Herold, K.C., et al. 2002. Anti-CD3 monoclonal antibody in new-onset type 1 diabetes mellitus. N Engl J Med 346:1692-1698.
Hill, G.R., et al. 1997. Total body irradiation and acute graft-versus-host disease: the role of gastrointestinal damage and inflammatory cytokines. Blood 90:3204-3213.
Ianus, A., Holz, G.G., Theise, N. D., Hussain, M.A. 2003. In vivo derivation of glucose-competent pancreatic endocrine cells from bone marrow without evidence of cell fusion. J Clin Invest 111:843-850.
Kaufman, C.L., Li, H., Ildstad, S.T. 1997. Patterns of hemopoietic reconstitution in nonobese diabetic mice: dichotomy of allogeneic resistance versus competitive advantage of disease-resistant marrow[1]. J Immunol 158:2435-2442.
Kim, Y.M., et al. 2003. Graft-versus-host disease can be separated from graft-versus-lymphoma effects by control of lymphocyte trafficking with FTY720. J Clin Invest 111:659-669.
Kim, Y.M., et al. 2004. Graft-versus-host-reactive donor CD4 cells can induce T cell-mediated rejection of the donor marrow in mixed allogeneic chimeras prepared with nonmyeloablative conditioning. Blood 103:732-739.
Kodama, S., et al. 2003. Islet regeneration during the reversal of autoimmune diabetes in NOD mice. Science 302:1223-1227.
Kronenberg, M., Gapin, L. 2002. The unconventional lifestyle of NKT cells. Nat Rev Immunol 2:557-568.
Kunkel, E.J., et al. 2000. Lymphocyte CC chemokine receptor 9 and epithelial thymus-expressed chemokine (TECK) expression distinguish the small intestinal immune compartment: Epithelial expression of tissue-specific chemokines as an organizing principle in regional immunity. J Exp Med 192:761-767.
Lan, F., et al. 2001. Predominance of NK1.1$^+$TCR alpha beta$^+$ or DX5$^+$TCR alpha beta$^+$ T cells in mice conditioned with fractionated lymphoid irradiation protects against graft-versus-host disease: "natural suppressor" cells[1]. J Immunol 167:2087-2096.
Li, H., et al. 1996. Mixed allogeneic chimerism induced by a sublethal approach prevents autoimmune diabetes and reverses insulitis in nonobese diabetic (NOD) mice[1]. J Immunol 56:380-388.
Loetscher, P., et al. 1998. CCR5 is characteristic of Th1 lymphocytes. Nature 391:344-345.
Martin, P.J. 1993. Donor CD8 cells prevent allogeneic marrow graft rejection in mice: potential implications for marrow transplantation in humans. J Exp Med 178:703-712.
Martin, P.J., et al. 1999. A phase I-II clinical trial to evaluate removal of CD4 cells and partial depletion of CD8 cells from donor marrow for HLA-mismatched unrelated recipients. Blood 94:2192-2199.
Murai, M., et al. 1999. Active participation of CCR5$^+$CD8$^+$ T lymphocytes in the pathogenesis of liver injury in graft-versus-host disease. J Clin Invest 104:49-57.
Nakajima, C., et al. 2002. Induction of the chemokine receptor CXCR3 on TCR-stimulated T cells: dependence on the release from persistent TCR-triggering and requirement for IFN-gamma stimulation. Eur J Immunol 32:1792-1801.
Nikolic, B., et al. 2004. Mixed hematopoietic chimerism allows cure of autoimmune diabetes through allogeneic tolerance and reversal of autoimmunity. Diabetes 53:376-383.
Olson, T.S., Ley, K. 2002. Chemokines and chemokine receptors in leukocyte trafficking. Am J Physiol Regul Integr Comp Physiol 283:R7-28.
Patterson, B.K., et al. 1999. Regulation of CCR5 and CXCR4 expression by type 1 and type 2 cytokines: CCR5 expression is downregulated by IL-10 in CD4-positive lymphocytes. Clin Immunol 91:254-262.
Pelot, M.R., et al. 1999. Lymphohematopoietic graft-vs.-host reactions can be induced without graft-vs.-host disease in murine mixed chimeras established with a cyclophosphamide-based nonmyeloablative conditioning regimen. Biol Blood Marrow Transplant 5:133-143.
Picker, L.J., Michie, S.A., Rott, L.S., Butcher, E.C. 1990. A unique phenotype of skin-associated lymphocytes in humans. Preferential expression of the HECA-452 epitope by benign and malignant T cells at cutaneous sites. Am J Pathol 136:1053-1068.
Ricordi, C. 2003. Islet transplantation: a brave new world. Diabetes 52:1595-1603.
Rossini, A.A. 2004. Autoimmune diabetes and the circle of tolerance. Diabetes 53:267-275.
Seung, E., et al. 2000. Allogeneic hematopoietic chimerism in mice treated with sublethal myeloablation and anti-CD154 antibody: absence of graft-versus-host disease, induction of skin allograft tolerance, and prevention of recurrent autoimmunity in islet-allografted NOD/Lt mice. Blood 95:2175-2182.
Seung, E., Mordes, J.P., Rossini, A.A., Greiner, D.L. 2003. Hematopoietic chimerism and central tolerance created by peripheral-tolerance induction without myeloablative conditioning. J Clin Invest 112:795-808.
Shlomchik, W.D., et al. 1999. Prevention of graft versus host disease by inactivation of host antigen-presenting cells. Science 285:412-415.
Soiffer, R.J. 2004. T-cell depletion to prevent Graft-vs-Host Disease. Hematopoietic cell transplantation. Malden: Blackwell Science Ltd. 221-233.
Sullivan, K.M., Furst, D.E. 1997. The evolving role of blood and marrow transplantation for the treatment of autoimmune diseases. J Rheumatol Suppl 48:1-4.
Sullivan, K.M. 2004. Graft-vs-host desease. Hematopoietic cell transplantation. Malden: Blackwell Science Ltd. 635-664.
Sykes, M., Sheard, M.A., Sachs, D.H. 1988. Graft-versus-host-related immunosuppression is induced in mixed chimeras by alloresponses against either host or donor lymphohematopoietic cells. J Exp Med 168:2391-2396.
Sykes, M. 2001. Mixed chimerism and transplant tolerance. Immunity 14:417-424.
Sykes, M. 2004. Mechanisms of Tolerance. Hematopoietic Cell Transplantation. Malden: Blackwell Science Ltd. 300-323.
Taniguchi, M., et al. 2003. The regulatory role of Valpha14 NKT cells in innate and acquired immune response. Annu Rev Immunol 21:483-513.
Teshima, T., et al. 2002. Acute graft-versus-host disease does not require alloantigen expression on host epithelium. Nat Med 8:575-581.
Todorov, I.T., Attaran, A., Kearsey, S.E. 1995. BM28, a human member of the MCM2-3-5 family, is displaced from chromatin during DNA replication. J Cell Biol 129:1433-1445.
Wagner, J.L., et al. 1998. The development of chronic graft-versus-host disease: an analysis of screening studies and the impact of corticosteroid use at 100 days after transplantation. Bone Marrow Transplant 22:139-146.
Wekerle, T., et al. 2000. Allogeneic bone marrow transplantation with co-stimulatory blockade induces macrochimerism and tolerance without cytoreductive host treatment. Nat Med 6:464-469.
Zeng, D., et al 1999. Bone marrow NK1.1$^-$ and NK1.1$^+$ T cells reciprocally regulate acute graft versus host disease. J Exp Med 189:1073-1081.
Zeng, D., et al. 2000. Cutting edge: a role for CD1 in the pathogenesis of lupus in NZB/NZW mice[1]. J Immunol 164:5000-5004.
Zeng, D., et al. 2002. Unique patterns of surface receptors, cytokine secretion, and immune functions distinguish T cells in the bone marrow from those in the periphery: impact on allogeneic bone marrow transplantation. Blood 99:1449-1457.
Zeng, D., et al. 2003a. Different patterns of migration and expansion of blood and marrow CD4 T cells in lymphoid and non-lymphoid tissues result in a different capacity to induce Graft-vs-Host Disease. The American Association of Immunologists 90th Anniversary Annual Meeting. Denver, Colorado: FASEB C59.
Zeng, D., et al. 2003b. Activation of natural killer T cells in NZB/W mice induces Th1-type immune responses exacerbating lupus. J Clin Invest 112:1211-1222.
Zeng, D., et al. 2004. Suppression of graft-versus-host disease by naturally occurring regulatory T cells. Transplantation 77:S9-S11.

Yoshida, A., et al., 2004. CD8 T Cell of Donor Splenocyte Mixed with Bon Marrow Cells is More Effective Than CD4 T Cell for Induction of Donor-Specific Tolerance in Sublethally Irradiated Mice. Transplantation Proceedings 36:2418-2422.

Itabashi, Y., et al., 2002. Allogeneic Chimerism established with a mixture of low does bone marrow cells and splenocytes in sublethally irradiated mice. Transplant Immunology 10:25-30.

Agata, Y., et al., "Expression of the PD-1 Antigen on the Surface of Stimulated Mouse T and B Lymphocytes," Int. Immunol. 8:765-772 (1996).

Alegre, M., et al., "Hypothennia and Hypoglycemia Induced by Anti-CD3 Monoclonal Antibody in Mice: Role of Tumor Necrosis Factor," Eur J Immunol 20:707-710 (1990).

Alegre, M.L., et al., "Cytokine Release Syndrome Induced by the 145-2C11 Anti-CD3 Monoclonal Antibody in Mice: Prevention by High Doses of Methylpresdnisolone," J. Immunol. 146(4): 1184-1191 (1991).

Appelbaum, F. R., "Haematopoietic Cell Transplantation as Immunotherapy," Nature 411:385-389 (2001).

Beaty, S. R., et al., "Diverse and Potent Chemokine Production by Lung CD11b$^{high}$ Dendritic Cells in Homeostasis and in Allergic Lung Inflammation," J. Immunol. 178:1882-1895 (2007).

Beilhack, A., et al., "In Vivo Analyses of Early Events in Acute Graft-Versus-Host Disease Reveal Sequential Infiltration of T-Cell Subsets," Blood 106:1113-1122 (2005).

Beilhack, A., et al., "Prevention of Acute Graft-Versus-Host Disease by Blocking T-Cell Entry to Secondary Lymphoid Organs," Blood 111:2919-2928 (2008).

Blazar, B. R., et al., "Blockade of Programmed Death-1 Engagement Accelerates Graft-Versus-Host Disease Lethality by an IFN-γ-Dependent Mechanism," J. Immunol. 171:1272-1277 (2003).

Burman, A. C., et al., "IFN{gamma} Differentially Controls the Development of Idiopathic Pneumonia Syndrome and GVHD of the Gastrointestinal Tract," Blood 110:1064-1072 (2007).

Cao, Y.A., et al., "Shifting Foci of Hematopoiesis During Reconstitution from Single Stem Cells," PNAS 101:221-226 (2004).

Chakraverty, R., et al., "An Inflammatory Checkpoint Regulates Recruitment of Graft-Versus-Host Reactive T Cells to Peripheral Tissues," J. Exp. Med. 203:2021-2031 (2006).

Chakraverty, R., et al., "The Role of Antigen-Presenting Cells in Triggering Graft-Versus-Host Disease and Graft—Versus—Leukemia," Blood 110:9-17 (2007).

Chatenoud, L., et al., "CD3-Specific Antibodies: A Portal to the Treatment of Autoimmunity," Nat. Rev. Immunol. 7:622-632 (2007).

Chen, L., et al., "Co-Inhibitory Molecules of the B7-CD28 Family in the Control of T-Cell Immunity," Nat. Rev. Immunol. 4:336-347 (2004).

Cooke, K. R., et al., "An Experimental Model of Idiopathic Pneumonia Syndrome After Bone Marrow Transplantation: I. The Roles of Minor H Antigens and Endotoxin," Blood 88:3230-3239 (1996).

Cooke, K. R., et al., "LPS Antagonism Reduces Graft-Versus-Host Disease and Preserves Graft-Versus-Leukemia Activity After Experimental Bone Marrow Transplantation," J. Clin. Invest. 107:1581-1589 (2001).

Coombes, J. L., et al., "A Functionally Specialized Population of Mucosal CD103$^+$ DCs Induces Foxp3$^+$ Regulatory T Cells Via a Tgf-β- and Retinoic Acid-Dependent Mechanism," J. Exp. Med. 8:1757-1764 (2007).

Decalf, J., et al., "Plasmacytoid Dendritic Cells Initiate a Complex Chemokine and Cytokine Network and Are a Viable Drug Target in Chronic HCV Patients," J. Exp. Med. 204:2423-2437 (2007).

Dong, H., et al., "B7-H1 Determines Accumulation and Deletion of Intrahepatic CD8$^+$ T Lymphocytes," Immunity 20:327-336 (2004).

Dong, H., et al., "Tumor-Associated B7-H1 Promotes T-Cell Apoptosis: A Potential Mechanism of Immune Evasion," Nat. Med. 8:793-800 (2002).

Drakes, M. L., et al., "Isolation and Purification of Colon Lamina Propria Dendritic Cells from Mice with Colitis," Cytotechnology 46:151-161 (2004).

Duffner, U. A., et al., "Host Dendritic Cells Alone are Sufficient to Initiate Acute Graft-Versus-Host Disease," J. Immunol. 172:7393-7398 (2004).

Duffner, U., et al., "Role of CXCR3-Induced Donor T-Cell Migration in Acute GVHD," Exp. Hematol. 31:897-902 (2003).

Fife, B. T., et al., "Control of Peripheral T-Cell Tolerance and Autoimmunity Via the CTLA-4 and PD-1 Pathways," Immunol. Rev. 224:166-182 (2008).

Giralt, S., "Reduced-Intensity Conditioning Regimens for Hematologic Malignancies: What Have We Learned Over the Last 10 Years?" Hematology Am. Soc. Hematol. Educ. Program 384-389 (2005).

Greenwald, R. J., et al., "The B7 Family Revisited," Annu. Rev. Immunol. 23:515-548 (2005).

Haspot, F., et al., "Peripheral Deletional Tolerance of Alloreactive CD8 But Not CD4 T Cells is Dependent on the PD-1/PD-L1 Pathway," Blood 112:2149-2155 (2008).

Hieshima, K., et al., CC CHemokine Ligands 25 and 28 Play Essential Roles in Intestinal Extravasation of IfA Antibody-Secreting Cells, J. Immunol. 173:36683675 (2004).

Hildebrandt, G. C., et al., "Blockade of CXCR3 Receptor: Ligand Interactions Reduces Leukocyte Recruitment to the Lung and the Severity of Experimental Idiopathic Pneumonia Syndrome," J. Immunol. 173:2050-2059 (2004).

I Ishida, M., et al., "Differential Expression of PD-L1 and PD-L2, Ligands for an Inhibitory Receptor PD-1, in the Cells of Lymphohematopoietic Tissues," Immunol. Lett. 84:57-62 (2002).

Iwata, M., et al., "Retinoic Acid Imprints Gut-Homing Specificity on T Cells," Immunity 21:527-538 (2004).

Jaksch, M., et al., "Increased Gene Expression of Chemokine Receptors is Correlated with Acute Graft-Versus-Host Disease After Allogeneic Stem Cell Transplantation," Biol. Blood Marrow Transplant. 11:280-287 (2005).

Johansson-Lindbom, B., et al., "Functional Specialization of Gut CD103$^+$ Dendritic Cells in the Regulation of Tissue-Selective T cell Homing," J. Exp. Med. 202:1063-1073 (2005).

Johansson-Lindbom, B., et al., "Selective Generation of Gut Tropic T Cells in Gut-Associated Lymphoid Tissue (GALT): Requirement for GALT Dendritic Cells and Adjuvant," J. Exp. Med. 198:963-969 (2003).

Johnson, B. D., et al., "Use of Anti-CD3ε F(ab')$_2$ Fragments in Vivio to Modulate Graft-Versus-Host Disease Without Loss of Graft-Versus-Leukemia Reactivity After MHC-Matched Bone Marrow Transplantation," J. Immunol. 154:5542-5554 (1995).

Kaplan, D. H., et al., "Target Antigens Determine Graft-Versus-Host Disease Phenotype," J. Immunol. 173:5467-5475 (2004).

Keir, M. E., et al., "Tissue Expression of PD-L1 Mediates Peripheral T Cell Tolerance," J. Exp. Med. 203:883-895 (2006).

Kim, T. D., et al., "Organ-Derived Dendritic Cells have Differential Effects on Alloreactive T Cells," Blood 111:2929-2940 (2008).

Leng, C., et al., "Reduction of Graft-Versus-Host Disease by Histone Deacetylase Inhibitor Suberonylanilide Hydroxamic Acid is Associated with Modulation of Inflammatory Cytokine Milieu and Involves Inhibition of STAT1," Exp Hematol 34:776-87 (2006).

Leoni, F., et al., "The Antitumor Histone Deacetylase Inhibitor Suberoylanilide Hydroxamic Acid Exhibits Antiinflammatory Properties Via Suppression of Cytokines," Proc Natl Acad Sci USA 99:2995-3000 (2002).

Li, N., et al., "Anti-CD3 Preconditioning Separates GVL from GVHD Via Modulating Host Dendritic Cell and Donor T-Cell Migration in Recipients Conditioned with TBI," Blood 22:953-962 (2009).

Li, N., et al., "HDAC Inhibitor Reduces Cytokine Storm and Facilitates Induction of Chimerism that Reverses Lupus in Anti-CD3 Conditioning Regimen," PNAS 105:4796-4801 (2008).

Li, N., et al., "Histone Deacetylase Inhibitor SAHA Reduces Cytokine Storm and Facilitates Induction of Chimerism When Combined with Anti-CD3 mAb in Conditioning of Recipients," Blood 110(11):part 1, pp. 645A (2007).

Liang, Y., et al., "Donor CD8+ T Cells Facilitate Induction of Chimerism and Tolerance Without GVHD in Autoimmune NOD Mice Conditioned with Anti-CD3 mAb," Blood 105:2180-2188 (2005).

Mapara, M. Y., et al., "Expression of Chemokines in GVHD Target Organs Is Influenced by Conditioning and Genetic Factors and Amplified by GVHR," Biol. Blood Marrow Transplant. 12:623-634 (2006).

Marks, P., et al., "Histone Deacetylases and Cancer: Causes and Therapies," Nat Rev Cancer 1:194-202 (2001).

Marks, P.A., et al., "Histone Deacetylases," Curr Opin Pharmacol 3:344-51 (2003).

Marks, P. A., et al., "Histone Deacetylase Inhibitors: Discovery and Development as Anticancer Agents," Expert Opin. Investig. Drugs 14(12):1497-1511 (2005).

Marzo, A. L., et al., "Fully Functional Memory CD8 T Cells in the Absence of CD4 T Cells," J. Immunol. 173:969-975 (2004).

Merad, M., et al., "Depletion of Host Langerhans Cells Before Transplantation of Donor Alloreactive T Cells Prevents Skin Graft-Versus-Host Disease," Nat. Med. 10:510-517 (2004).

Mishra, N., et al., "Histone Deacetylase Inhibitors Modulate Renal Disease in the MRL-lpr/lpr Mouse," J Clin Invest 111:539-552 (2003).

Mora, J. R., et al., "Reciprocal and Dynamic Control of CD8 T Cell Homing by Dendritic Cells from Skin- and Gut-Associated Lymphoid Tissues," J. Exp. Med. 201:303-316 (2005).

Morris, E.S., et al., "NKT Cell—Dependent Leukemia Eradication Following Stem Cell Mobilization With Potent GCSF Analogs," J Clin Invest 115:3093-3103 (2005).

Mucida, D., et al., "Reciprocal $T_H17$ and Regulatory T Cell Differentiation Mediated by Retinoic Acid," Science 317:256-260 (2007).

Muhlbauer, M., et al., "Pd-L1 is Induced in Hepatocytes by Viral Infection and by Interferon-$\alpha$ and -$\gamma$ and Mediates T cell Apoptosis," J. Hepatol. 45:520-528 (2006).

Muraille, E., et al., "Downregulation of Antigen-Presenting Cell Functions After Administration of Mitogenic Anti-CD3 Monoclonal Antibodies in Mice," Blood 94:4347-4357 (1999).

Murphy, W. J., et al., "Differential Effects of the Absence of Interferon-$\gamma$ and IL-4 in Acute Graft-Versus-Host Disease After Allogenic Bone Marrow Transplantation in Mice," J. Clin. Invest. 102:1742-1748 (1998).

Nakazawa, A., et al., "The Expression and Function of Costimulatory Molecules B7h and B7-H1 on Colonic Epithelial Cells," Gastroenterol. 126:1347-1357 (2004).

Nishimura, H., et al., "Autoimmune Dilated Cardiomyopathy in PD-1 Receptor-Deficient Mice," Science 291:319-322 (2001).

Nishimura, H., et al., "Development of Lupus-Like Autoimmune Diseases by Disruption of the PD-1 Gene Encoding an ITIM Motif-Carrying Immunoreceptor," Immunity 11:141-151 (1999).

Ohl, L., et al., "CCR7 Governs Skin Dendritic Cell Migration Under Inflammatory and Steady-State Conditions," Immunity 21:279-288 (2004).

Panoskaltsis-Mortari, A., et al., "In Vivo Imaging of Graft-Versus-HostDisease in Mice," Blood 103:3590-3598 (2004).

Perruche, S., et al., "CD3-Specific Antibody-Induced Immune Tolerance Involves Transforming Growth Factor-$\beta$ from Phagocytes Digesting Apoptotic T Cells," Nat. Med. 14:528-535 (2008).

Reddy, P., et al., "A Crucial Role for Antigen-Presenting Cells and Alloantigen Expression in Graft-Versus-Leukemia Responses," Nat. Med. 11:1244-1249 (2005).

Reddy, P., et al., "Histone Deacetylase Inhibitor Suberoylanilide Hydroxamic Acid Reduces Acute Graft-Versus-Host Disease and Preserves Graft-Versus-Leukemia Effect," Proc Natl Acad Sci USA 101:3921-3926 (2004).

Reiss, Y., et al., "CC Chemokine Receptor (CCR)4 and the CCR10 Ligand Cutaneous T Cell-Attracting Chemokine (CTACK) in Lymphocyte Trafficking to Inflamed Skin," J. Exp. Med. 194:1541-1547 (2001).

Ringden, O., et al., "Low Incidence of Acute Graft-Versus-Host Disease, Using Unrelated HLA-A-, HLA-B-, and HLA-DR-Compatible Donors and Conditioning, Including Anti-T-Cell Antibodies," Transplantation 66(5):620-625 (1998).

Roth, S. Y., et al., "Histone Acetyltransferases," Annu Rev Biochem 70:81-120 (2001).

Sackstein, R., "A Revision of Billingham's Tenets: The Central Role of Lymphocyte Migration in Acute Graft-Versus-Host Disease," Biol. Blood Marrow Transplant. 12:2-8 (2006).

Schoop, R., et al., "Suppressed T-Cell Activation by IFN-$\gamma$-Induced Expression of PD-L1 on Renal Tubular Epithelial Cells," Nephrol. Dial. Transplant. 19:2713-2720 (2004).

Shlomchik, W. D., "Graft-Versus-Host Disease," Nat. Rev. Immunol. 7:340-352 (2007).

Shlomchik, W. D., et al., "Transplantation's Greatest Challenges: Advances in Chronic Graft-Versus-Host Disease," Biol. Blood Marrow Transplant. 13:2-10 (2007).

Sigmundsdottir, H., et al., "DCs Metabolize Sunlight-Induced Vitamin D3 to 'Program' T cell Attraction to the Epidermal Chemokine CCL27," Nat. Immunol. 8:285-293 (2007).

Slavin, S., et al., "Nonmyeloablative Stem Cell Transplantation and Cell Therapy as an Alternative to Conventional Bone Marrow Transplantation with Lethal Cytoreduction for the Treatment of Malignant and Nonmalignant Hematologic Diseases," Blood 91:756-763 (1998).

Smith-Berdan, S., et al., "Reversal of Autoimmune Disease in Lupus-Prone New Zealand Black/New Zealand White Mice by Nonmyeloablative Transplantation of Purified Allogeneic Hematopoietic Stem Cells," Blood 110:1370-1378 (2007).

Stenstad, H., et al., "Differential Homing Mechanisms Regulate Regionalized Effector $CD8\alpha\beta^+$ T cell Accumulation Within the Small Intestine," PNAS 104:10122-10127 (2007).

Sun, J. C., et al., "CD4+ T Cells are Required for the Maintenance, Not Programming, of Memory CD8+ T Cells After Acute Infection," Nat. Immunol. 5:927-933 (2004).

Sykes, M., et al., "Treatment of Severe Autoimmune Disease by Stem-Cell Transplantation," Nature 435:620-627 (2005).

Terwey, T. H., et al., "CCR2 is Required for CD8-Induced Graft-Versus-Host Disease," Blood 106:3322-3330 (2005).

Tietz, W., et al., "CD4+ T Cells Migrate into Inflamed Skin Only If They Express Ligands for E- and P-Selectin," J. Immunol. 161:963-970 (1998).

Turnbull, E. L., et al., "Intestinal Dendritic Cell Subsets: Differential Effects of Systemic TLR4 Stimulation on Migratory Fate and Activation in Vivo," J. Immunol. 174:1374-1384 (2005).

Varona, R., et al., "CCR6 Regulates CD4+ T-Cell-Mediated Acute Graft-Versus-Host Disease Responses," Blood 106:18-26 (2005).

Wakim, L. M., et al., "Dendritic Cell-Induced Memory T Cell Activation in Nonlymphoid Tissues," Science 319:198-202 (2008).

Webster, A. C., et al., "Monoclonal and Polyclonal Antibody Therapy for Treating Acute Rejection in Kidney Transplant Recipients: A Systematic Review of Randomized Trial Data," Transplantation 81:953-965 (2006).

Welniak, L. A., et al., "Immunobiology of Allogeneic Hematopoietic Stem Cell Transplantation," Annu. Rev. Immunol. 25:139-170 (2007).

Wysocki, C. A., et al., "Differential Roles for CCR5 Expression on Donor T Cells During Graft-Versus-Host Disease Based on Pretransplant Conditioning," J. Immunol. 173:845-854 (2004).

Wysocki, C. A., et al., "Leukocyte Migration and Graft-Versus-Host Disease," Blood 105:4191-4199 (2005).

Xu, W.S., et al., "Histone Deacetylase Inhibitors: Molecular Mechanisms of Action," Oncogene 26:5541-52 (2007).

Yamazaki, T., et al., "Expression of Programmed Death 1 Ligands by Murine T Cells and APC," J. Immunol. 169:5538-5545 (2002).

Yang, Y.G., et al., "Donor-Derived Interferon $\gamma$ Is Required for Inhibition of Acute Graft-Versus-Host Disease by Interleukin 12," J. Clin. Invest. 102:2126-2135 (1998).

Yang, F., et al., "Spontaneous Development of Liver Tumors in the Absence of the Bile Acid Receptor Farnesoid X Receptor," Cancer Res. 67:863-867 (2007).

Yi, T., et al., "Absence of Donor Th17 Leads to Augmented Th1 Differentiation and Exacerbated Acute Graft-Versus-Host Disease," Blood 112:2101-2110 (2008).

Youngnak-Piboonratanakit, P., et al., "The Expression of B7-H1 on Keratinocytes in Chronic Inflammatory Mucocutaneous Disease and Its Regulatory Role," Immunol. Lett. 94:215-222 (2004).

Yu, X.Z., et al., "CD28 Ligation Induces Transplantation Tolerance by IFN-$\gamma$-Dependent Depletion of T Cells that Recognize Alloantigens," J. Clin. Invest. 113:1624-1630 (2004).

Zhang, Y., et al., "APCs in the Liver and Spleen Recruit Activated Allogenic CD8+ T Cells to Elicit Hepatic Graft-Versus-Host Disease," J. Immunol. 169:7111-7118 (2002).

Zhang, C., et al., "Donor CD4+ T and B Cells in Transplants Induce Chronic Graft-Versus-Host Disease with Autoimmune Manifestations," Blood 107:2993-3001 (2006).

Zhang, C., et al., "Donor CD8+ T Cells Mediate Graft-Versus-Leukemia Activity Without Clinical Signs of Graft-Versus-Host Disease in Recipients Conditioned with Anti-CD3 Monoclonal Antibody," J. Immunol. 178:838-850 (2007).

Zhang, C., et al., "Elimination of Insulitis and Augmentation of Islet γ Cell Regeneration Via Induction of Chimerism in Overtly Diabetic NOD Mice," PNAS 104:2337-2342 (2007).

Zhao, D., et al., "In Vivo Activated CD103+CD4+ Regulatory T Cells Ameliorate Ongoing Chronic Graft-Versus-Host Disease," Blood 112:2129-2138 (2008).

* cited by examiner

COMPOSITIONS AND METHODS FOR INDUCING CHIMERISM IN A SUBJECT

CROSS-REFERENCE TO RELATED APPLICATIONS

The present utility application is a divisional of U.S. patent application Ser. No. 11/226,867, filed Sep. 13, 2005, now abandoned, which claims priority to U.S. Provisional Application No. 60/609,850, filed Sep. 13, 2004. The disclosure of each of these applications is incorporated by reference herein in their entirety, including drawings.

BACKGROUND

Type 1 diabetes is an autoimmune disease characterized by destruction of insulin-secreting pancreatic islet β cells by pathogenic autoreactive T cells (Castano 1990; Rossini 2004). The resultant decrease in insulin secretion leads to hyperglycemia. Type 1 diabetes has traditionally been managed by administering exogenous insulin, which delays the onset and progression of the microvascular complications associated with diabetes. However, insulin administration does not cure the disease. A more recently developed therapy is islet transplantation, in which faulty pancreatic islets are replaced with new insulin-producing islets. However, the underlying autoimmune disorder remains, meaning that the newly transplanted islets will continue to be attacked by the host immune system. This can be overcome using long-term immunosuppressive therapy, but this procedure is accompanied by a variety of deleterious side effects.

An alternative to immunosuppressive therapy is bone marrow transplantation (BMT), in which bone marrow from a non-autoimmune donor is transferred to the autoimmune host, leading to allogeneic hematopoietic chimerism. In a mouse model, BMT has been shown to reverse insulitis, prevent the development of diabetes, and induce tolerance to donor islet cells (Li 1996; Kaufman 1997; Seung 2000; Beilhack 2003; Nikolic 2004). However, BMT has several potential drawbacks. First, it requires conditioning of the host by non-myeloablative total body irradiation (TBI) (Li 1996; Kaufman 1997; Seung 2000; Beilhack 2003; Nikolic 2004), which is highly toxic. Second, it is often accompanied by the development of acute and chronic graft-versus-host disease (GVHD) (Exner 1997; Sullivan 1997; Burt 1998; Wagner 1998). The toxicity of TBI conditioning and the potential for GVHD have limited the application of BMT for the treatment of type 1 diabetes and the induction of immune tolerance to islet transplantation (Ricordi 2003). Administration of co-stimulatory blockade (anti-CD40L) has been reported to induce mixed chimerism in non-autoimmune mice (Wekerle 2000; Seung 2003). However, there is a need in the art for a radiation-free BMT regimen for the treatment of autoimmunity and induction of donor tolerance.

SUMMARY

In certain embodiments, compositions are provided comprising bone marrow cells and CD8+ T cells.

In certain embodiments, methods are provided for conditioning a recipient for bone marrow transplantation by administering a therapeutically effective amount of anti-CD3 mAb.

In certain embodiments, methods are provide for generating chimerism in a recipient by administering a therapeutically effective amount of anti-CD3 mAb, a therapeutically effective amount of donor bone marrow cells, and a therapeutically effective amount of donor CD8+ T cells. In certain of these embodiments, administration of donor bone marrow cells and donor CD8+ T cells occurs seven days after administration of anti-CD3 mAb. In certain embodiments, administration of donor bone marrow cells and donor CD8+ T cells is repeated, preferably 14 days after administration of anti-CD3 mAb.

DETAILED DESCRIPTION

Figure 1:
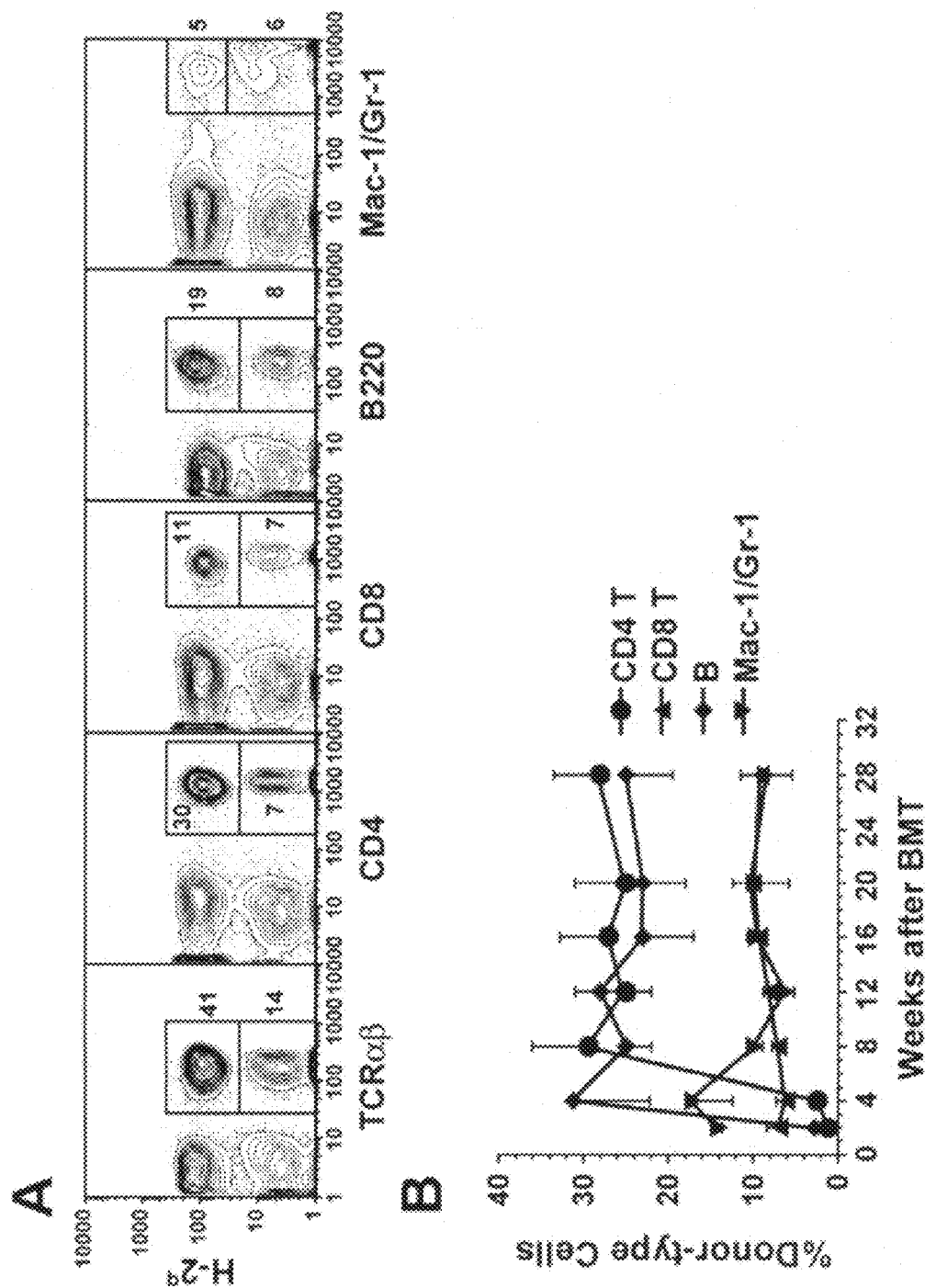
FIG. 1: Mixed-chimerism in anti-CD3 mAb-conditioned NOD recipients. A. Flow cytometric analysis of donor-type (H-$2^{q+}$) cells, including TCRαβ+, CD4+, CD8+, B220+, and Mac-1+/Gr-1+ cells, in blood mononuclear cells of anti-CD3 mAb-conditioned recipients 10 weeks after BMT. The percentage of H-$2^{q+}$ donor-type and H-$2^{q-}$ host-type cells are shown beside or in the gating boxes. Results are for a single representative of the twelve recipients. B. Stable multi-lineage chimerism in peripheral blood of NOD recipients was observed for more than 28 weeks after BMT. Values are mean±SE of twelve recipients combined from 3 experiments (n=12).

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Recent studies have shown that irradiation itself plays a critical role in the induction of GVHD following BMT, and that higher doses of irradiation are associated with more severe GVHD. Disclosed herein are various compositions and methods for establishing chimerism via BMT without inducing GVHD.

The term "recipient" or "host" as used herein refers to a subject receiving transplanted or grafted tissue. These terms may refer to, for example, a subject receiving an administration of donor bone marrow, donor T cells, or a pancreatic islet graft. The transplanted tissue may be derived from a syngeneic or allogeneic donor.

The term "donor" as used herein refers to a subject from whom tissue is obtained to be transplanted or grafted into a recipient or host. For example, a donor may be a subject from whom bone marrow, T cells, or other tissue to be administered to a recipient or host is derived.

The term "chimerism" as used herein refers to a state in which one or more cells from a donor are present and functioning in a recipient or host. Recipient tissue exhibiting "chimerism" may contain donor cells only (complete chimerism), or it may contain both donor and host cells (mixed chimerism). "Chimerism" as used herein may refer to either transient or stable chimerism.

The phrase "therapeutically effective amount" as used herein refers to an amount of a compound that produces a desired therapeutic effect. For example, a therapeutically effective amount of anti-CD3 mAb may refer to that amount that results in depletion of recipient T cells, while a therapeutically effective amount of donor BM cells or donor CD8$^+$ T cells may refer to that amount that generates chimerism in a recipient. The precise therapeutically effective amount is an amount of the composition that will yield the most effective results in terms of efficacy in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy (Gennaro ed. 20$^{th}$ edition, Williams & Wilkins PA, USA) (2000).

The term "simultaneously" as used herein with regards to administration of two or more compounds means that the compounds are administered at the same or nearly the same time. For example, two or more compounds are considered to be administered "simultaneously" if they are administered via a single combined administration, two or more administrations occurring at the same time, or two or more administrations occurring in succession.

The following abbreviations are used herein: APC, antigen-presenting cell; BM, bone marrow; BMT, bone marrow transplantation; FACS, fluorescence-activated cell sorting; FcR, Fc receptor; FITC, fluorescein; GVHD, graft-versus-host disease; LPS, lipopolysaccharide; mAb, monoclonal antibody; NKT, natural killer T; NOD, non-obese diabetic; PBMNC, peripheral blood mononuclear cell; TBI, total body irradiation; TCD, T cell depleted.

GVHD in TBI conditioned recipients is caused by both TBI conditioning procedures and donor T cell attack of host epithelial tissues such as gut, skin and liver (Sullivan 2004). TBI conditioning plays a critical role in initiating the tissue damage and inflammatory cascade, and higher doses of TBI are associated with more severe GVHD (Hill 1997; Gonzalez 2002; Ferrara 2004). Host tissue damaged by TBI releases inflammatory cytokines (e.g., TNF-α, IL-6, IL-1) and chemokines. Additionally, the gut tissue damage caused by TBI allows the release of lipopolysaccharide (LPS) from intestinal flora, which induces a wide range of secondary inflammatory actions. Release of inflammatory cytokines and chemokines induces the maturation and activation of host antigen presenting cells (APC's), and these activated APC's in turn activate donor T cells (Shlomchik 1999). Activated donor T cells upregulate chemokine receptors in response to inflammatory chemokines and cytokines, migrate to inflammatory epithelial tissues, and differentiate into Th$_1$ and Tc$_1$ cells. Th$_1$ cells release inflammatory cytokines such as IFN-γ and TNF-α, which further enhances local inflammation, while Tc$_1$ cells attack host tissue (Ferrara 2004).

GVHD in TBI-conditioned recipients can be prevented by depletion of donor T cells, but this procedure markedly increases engraftment failure (Soiffer 2004). This is because donor CD8$^+$ T cells play a critical role in facilitating engraftment in both murine and human BMT recipients, despite the fact that they contribute to GVHD induction in TBI-conditioned recipients (Martin 1993; Martin 1999; Zeng 2002). It has been reported previously that donor T cell infusion after the waning of the inflammatory response induced by TBI-conditioning can convert mixed chimerism into complete chimerism without causing GVHD, and that donor CD8$^+$ T cells play a critical role in this conversion (Sykes 1988; Pelot 1999; Kim 2004). However, the ability of T cells to facilitate engraftment in non-TBI conditioned hosts has not been previously examined.

A series of experiments, described below, were performed to determine whether CD8+ T cells can facilitate donor stem cell engraftment in non-irradiated recipients without causing GVHD. It was unexpectedly found that administration of donor CD8+ T cells in combination with donor BM cells induced stable mixed chimerism without GVHD in non-irradiated NOD mice preconditioned with anti-CD3 mAb. The prevention of GVHD in anti-CD3 mAb-conditioned recipients was associated with low-level production of inflammatory cytokines (e.g., TNF-α), high-level production of anti-inflammatory cytokines (e.g., IL-4 and IL-10), and confinement of donor CD8+ T cell expansion to lymphohematopoietic tissues. Chimeric recipients displayed donor-specific tolerance, reversal of insulitis, and resistance to diabetes development.

In the experiments described herein, it has been shown that high doses of donor CD8+ T cells can overcome resistance in anti-CD3 mAb-conditioned NOD recipients and facilitate the engraftment of donor stem cells. The same dose of donor CD8+ T and BM cells induces severe lethal GVHD in recipients conditioned with sublethal TBI. Compared to TBI-conditioned NOD recipients, anti-CD3 mAb-conditioned NOD recipients have markedly lower levels of serum TNF-α, and markedly higher levels of serum IL-4 and IL-10. It has been previously reported that proinflammatory cytokine TNF-α plays a critical role in the induction of GVHD in TBI-conditioned recipients (Teshima 2002; Ferrara 2004).

Both donor and host type T cells are observed in the liver of anti-CD3 mAb-conditioned recipients, while only donor-type T cells are observed in the liver of TBI-conditioned recipients. More than 70% of host-type CD4+ T cells in the liver of anti-CD3 mAb-conditioned recipients are NKT cells. The yield of donor CD8+ T cells from the spleen of anti-CD3 mAb-conditioned recipients is significantly higher than from the spleen of TBI-conditioned recipients, but the yield of donor CD8+ T cells in the liver of anti-CD3 mAb-conditioned recipients is 10-fold lower than that of TBI-conditioned recipients. In addition, no lymphocyte infiltration is observed in the skin and gut tissues of chimeric recipients conditioned with anti-CD3 mAb. In contrast, severe lymphocyte infiltration is observed in these same tissues in chimeric recipients conditioned with TBI. These results indicate that donor CD8+ T cells in the anti-CD3 mAb-conditioned recipients expand predominantly in host lymphohematopoietic tissues such as spleen and lymph nodes. In contrast, donor CD8+ T cells in TBI-conditioned recipients expand in both lymphohematopoietic tissues and GVHD target tissues such as skin, gut, and liver. In previous reports, GVHD was prevented by confining donor T cells in the lymphohematopoietic tissues (Lan 2001; Zeng 2002; Kim 2003; Zeng 2003a).

Chemokine receptors play an important role in T cell trafficking (Olson 2002; Campbell 2003). CCR9 and CCR10 are critical for T cell migration to gut and skin, respectively (Picker 1990; Kunkel 2000), while CCR5 and CXCR3 play critical roles in liver GVHD injury and graft rejection (Loestscher 1998; Murai 1999; Hancock 2000; Zeng 2003a. On the other hand, expression of chemokine receptors on T cells is regulated by both chemokines and cytokines (Hancock 2001; Nakajima 2002; Olson 2002). For example, CXCR3 expression is regulated by chemokine IP-10 and cytokine IFN-γ (Hancock 2001; Nakajima 2002). CCR5 and CXCR4 expression on T cells is up-regulated by IFN-γ, but down-regulated by IL-4 and IL-10 (Annunziato 1999; Patterson 1999). Without wishing to be bound by any theory, the inventor postulates that in TBI-conditioned recipients, donor CD8+ T cells up-regulate chemokine receptors (e.g., CCR5, CCR9, CCR10, and CXCR3) in response to high levels of inflammatory chemokines and cytokines. These T cells than migrate to epithelial tissues such as skin, gut, and liver to cause GVHD. In anti-CD3 mAb-conditioned recipients, on the other hand, low-level production of inflammatory cytokines and chemokines and high-level production of IL-4 and IL-10 cytokines from NKT cells prevents the up-regulation of chemokine receptors on the donor CD8+ T cells. Because of this, these T cells are retained in the lymphohematopoietic tissues. Subsequently, the injected donor CD8+ T cells may become apoptotic and anergic in the non-irradiated recipients as reported previously (Gonzalez 2002). Therefore, donor CD8+ T cells facilitate donor stem cell engraftment without GVHD in anti-CD3 mAb-conditioned recipients, but induce GVHD in TBI-conditioned recipients.

Anti-CD3 mAbs are potent immunosuppressive agents. The purpose of anti-CD3 mAb-conditioning disclosed herein is to temporarily deplete host T cells that reject donor cells. This procedure differs from previous reports in which anti-CD3 mAb was used to prevent GVHD by depleting or blocking donor T cell function in TBI-conditioned recipients (Blazar 1994; Blazar 1997).

Multiple injections of non-depleting anti-CD3 mAb have been reported to ameliorate diabetes in NOD mice and diabetic patients, and this therapy was associated with an increase of $CD25^+CD4^+$ regulatory T cells that suppress autoimmunity (Herold 2002; Belghith 2003; Bluestone 2003). In the present disclosure, NOD mice conditioned with one injection of depleting anti-CD3 mAb did not show any increase of $CD25^+CD4^+$ T cells during the period of T cell recovery. In addition to depleting anti-CD3 mAb, it is contemplated that non-FcR-binding and non-depleting anti-CD3 mAb may be used to condition BMT recipients.

Veto cells in donor BM have been reported to facilitate engraftment and prevention GVHD in BMT models (Gandy 1999; Sykes 2004), but high doses of BM alone failed to induce stable chimerism in anti-CD3 mAb-conditioned NOD recipients. This indicates that the role of veto cells in the present regimen is minimal.

NOD recipients with long-term mixed chimerism display reversal of insulitis and resistance to diabetes development despite the presence of a high percentage (about 30%) of host-type T cells. The origin of these host-type T cells is not yet clear, but it is speculated that they are de novo developed host T cells after BMT, and they are not autoreactive. It is further hypothesized that anti-CD3 mAb-conditioning and injected donor CD8+ T cells eliminate host mature T cells in the lymphohematopoietic tissues, and that donor-derived cells (e.g., dendritic cells) restore the negative selection function in NOD thymus and delete the autoreactive T cells. This results in de novo developed host T cells after BMT that are tolerant to islet antigens. FVB/N donor superantigen mediated deletion of NOD host T cells was observed in long-term chimeric recipients. This mechanism of restoration of self-tolerance in chimeric NOD recipients has also been proposed in the previous reports (Beilhack 2003; Nikolic 2004).

It has been reported previously that islet cells in diabetic mice can be regenerated to reverse overt diabetes by either self-duplication or stem cell differentiation once self-tolerance has been restored (Ianus 2003; Kodama 2003; Dor 2004). It is contemplated that induction of mixed chimerism in diabetic NOD mice can promote the regeneration of islet cells and reversal of diabetes.

In conclusion, a radiation-free regimen has been developed that induces mixed chimerism in autoimmune NOD mice by taking advantage of donor CD8+ T cell function in facilitation of donor stem cell engraftment. The separation of engraftment facilitation and GVHD mediated by donor CD8+ T cells in non-irradiated recipients constitutes a novel approach for induction of mixed chimerism and immune tolerance. This approach will be useful in the treatment of various autoimmune disorders such as type 1 diabetes, and in the induction of tolerance for islet transplantation.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLES

Example 1

Method of Producing Chimerism in Anti-CD3 mAb-Conditioned Recipients using Donor BM and Donor CD8+ T Cells The non-obese diabetic (NOD) mouse represents an ideal animal model for human type 1 diabetes (Atkinson 1999). Female NOD mice develop insulitis at about 4 weeks of age, and begin to show diabetes from about 15 weeks of age (Atkinson 1999). Female NOD/LtJ ($H-2^{g7}$), FVB/N ($H-2^q$), B10A($H-2^a$), C57BL/6 ($H-2^b$), and BALB/c ($H-2^d$) mice were obtained at age 6-8 weeks (Jackson Laboratory, Bar Harbor, Me.) and maintained in a pathogen free room at City of Hope Research Animal Facilities (Duarte, Calif.).

Anti-CD3 mAbs (145-2C11) were purified from hybridoma (ATCC Number CRL-1975) culture supernatant using protein G columns as described previously (Zeng 2000; Zeng 2003b). At age 8-12 weeks, NOD/LtJ, C57BL/6, and BALB/c mice received an intravenous injection of this anti-CD3 mAb at a dose of 500 μg/mouse. TCRαβ+ T cells in all tissues (blood, spleen, lymph node, liver, BM, and thymus) were depleted one week after anti-CD3 treatment, partially recovered by two weeks, and completely recovered to pre-treatment levels by three to four weeks. As a result, five to ten days after antibody treatment was deemed a preferred time for donor cell infusion, with seven days being a more preferred time.

Seven days after anti-CD3 mAb injection, mice received an intravenous injection of $200 \times 10^6$ donor BM cells, either alone or in combination with $200 \times 10^6$ spleen CD8+ T cells from FVB/N ($H-2^q$). Following injection, mice were tested for chimerism by flow cytometric analysis of donor-type $H-2^{q+}$ cells in peripheral blood. Multiple-color FACS analysis and sorting were performed at City of Hope FACS facility using a 4-laser MOFLO immunocytometry system (Dako Cytomation, Fort Collins, Colo.), and data was analyzed using FLOWJO software (Tree Star, San Carlos, Calif.) as described previously (Zeng 2003b). Mice receiving donor BM, whether alone or in combination with CD8+ T cells, displayed low levels (5-10%) of chimerism with donor cells for the first 4 weeks following injection. This chimerism disappeared entirely by 8 weeks. This established that a single injection of donor BM or BM plus CD8+ T cells resulted in only transient chimerism in recipients conditioned with anti-CD3.

Based on these findings, mice in subsequent experiments received two intravenous injections of BM or BM plus CD8+ T cells. The first was at seven days after anti-CD3 mAb injection, while the second was at fourteen days after anti-CD3 mAb injection. Two injections of donor BM alone still resulted in transient chimerism, but two injections of donor BM plus CD8+ T cells resulted in stable long-term chimerism lasting more than 28 weeks after BMT in 90% (18/20) of recipients (FIG. 1). Chimerism was measured by staining recipient blood mononuclear cells with anti-donor $H-2^q$ versus anti-TCRαβ, CD4, CD8, B220, and Mac-1/Gr-1 (BD Pharmingen, San Diego, Calif.) and performing flow cytometric analysis (FIG. 1A). The percentage of each subset of donor-type cell among recipient blood mononuclear cells reached a stable level eight weeks after BMT, with approximately 25% CD4+ T cells, 8% CD8+ T cells, 22% B lymphocytes and 7% granulocytes/macrophage cells, for a total of approximately 60% (FIG. 1B). Long-term chimeric recipients (24 weeks after BMT) exhibited mixed chimerism in thymus, blood, spleen, lymph node, and bone marrow.

Various dosages of donor CD8+ T and BM cells were tested for their ability to induce chimerism. A single injection of $200 \times 10^6$ donor BM cells in combination with two injections of $10 \times 10^6$ donor CD8+ T cells induced long-term (>20 weeks) mixed chimerism in all (8/8) recipients. A single injection of $100 \times 10^6$ donor BM cells in combination with two injections of $5 \times 10^6$ donor CD8+ T cells induced long-term mixed chimerism in 63% (5/8) of recipients. Results for each dosage combination tested are presented in Table 1. As seen in the Table, donor-type cells such as T, B, and granulocyte/macrophage cells accounted for more than 35% of total blood mononuclear cells. The Table also shows that induction of mixed chimerism by donor BM and donor CD8+ T cells in anti-CD3 conditioned recipients was not dependent on a particular donor/recipient strain combination. C57BL/6 donor cells induced mixed chimerism in 100% of BALB/c recipients, while B10A donor cells induced chimerism in 100% of C57BL/6 recipients.

TABLE 1

| Donor | Donor CD8+ T cell dose (# of injections in parentheses) | Donor BM dose (# of injections in parentheses) | Recipient | % chimeric recipients | % donor-type cells in PBMNC |
|---|---|---|---|---|---|
| FVB/N | $20 \times 10^6$ (2) | $200 \times 10^6$ (2) | NOD | 90% (18/20) | 43.7-69.6% |
| FVB/N | $10 \times 10^6$ (2) | $200 \times 10^6$ (1) | NOD | 100% (8/8) | 39.7-57.5% |
| FVB/N | $5 \times 10^6$ (2) | $100 \times 10^6$ (1) | NOD | 63% (5/8) | 34.8-51.4% |
| C57BL/6 | $10 \times 10^6$ (2) | $200 \times 10^6$ (1) | BALB/c | 100% (8/8) | 45.6-71.3% |
| B10A | $10 \times 10^6$ (2) | $200 \times 10^6$ (1) | C57BL/6 | 100% (8/8) | 50.1-78.1% |

Example 2

Figure 2:
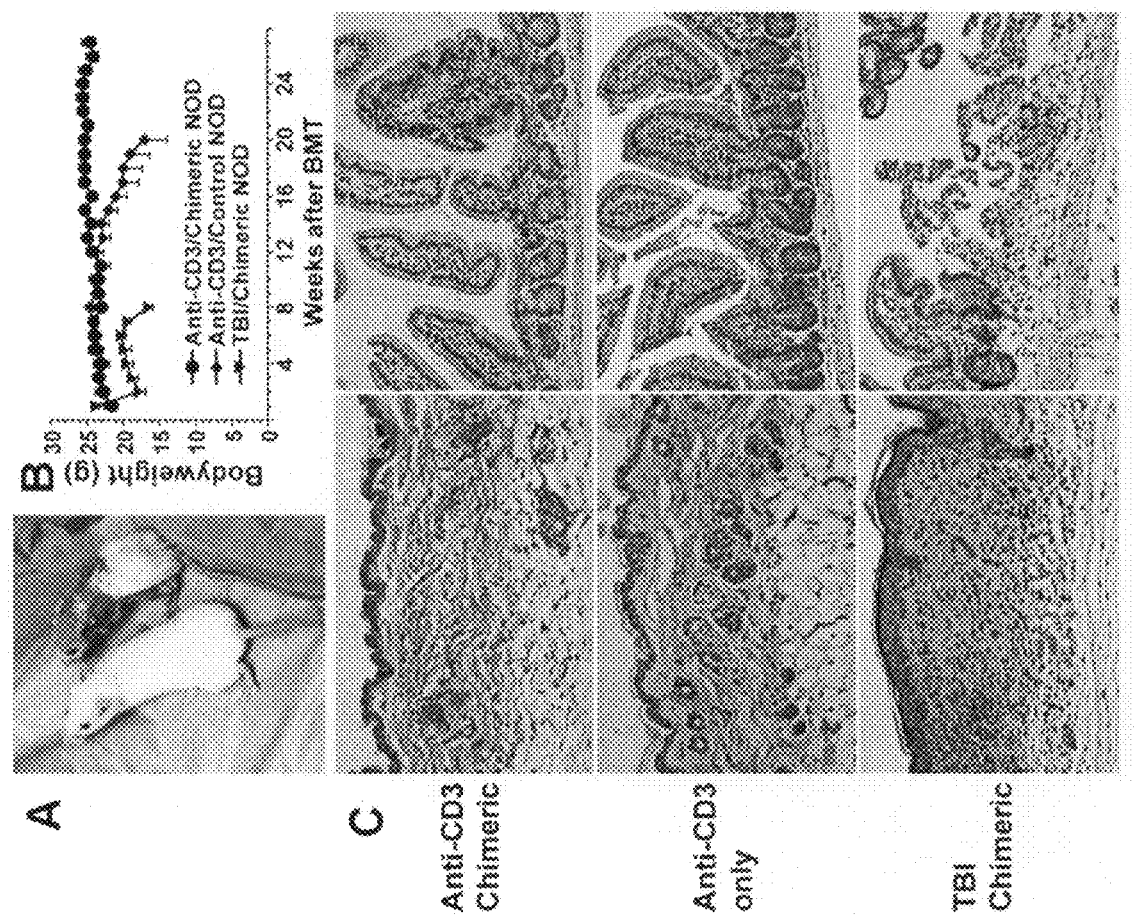
FIG. 2: Absence of GVHD in anti-CD3 mAb-conditioned chimeric recipients. A. The mouse on the left is representative of the GVHD-free chimeric recipients conditioned with anti-CD3 mAb. The mouse on the right is representative of the recipients conditioned with TBI. B. Change in body weight change of chimeric recipients over 28 weeks following BMT. Values are mean±SE for twelve chimeric recipients conditioned with anti-CD3 mAb, twelve control recipients conditioned with anti-CD3 mAb but receiving no BMT, and eight chimeric recipients conditioned with TBI. C. Histology of skin and small intestine tissues from chimeric recipients conditioned with anti-CD3 mAb, control recipients conditioned with anti-CD3 mAb but receiving no BMT, and chimeric recipients conditioned with TBI. Tissue samples were obtained at 50 days after BMT. Results are shown for a single representative of four examined from each group.

Absence of GVHD in Chimeric Recipients Generated Using Donor BM and Donor CD8+ T Cells The major concern with regards to donor CD8+ T cell infusion is GVHD, since donor peripheral CD8+ T cells induce severe GVHD in recipients conditioned with TBI (Martin 1999: Zeng 2002). Anti-CD3 mAb-conditioned chimeric recipients generated using the method set forth in Example 1 were carefully monitored for clinical signs of GVHD as described previously (Zeng 1999; Zeng 2002). These recipients showed no clinical signs of GVHD (e.g., no weight-loss, hair-loss, or diarrhea), remaining healthy over a follow-up period of more than 24 weeks after BMT (FIG. 2A, mouse on left; FIG. 2B). In contrast, eight mice conditioned with sublethal TBI (650 rads) and injected with $200 \times 10^6$ BM and $20 \times 10^6$ CD8+ T cells from FVB/N donors all developed severe clinical signs of GVHD, including weight-loss, hair-loss, hunched-back, and diarrhea (FIG. 2A, mouse on right; FIG. 2B). These eight mice were moribound 40-60 days after BMT. Control mice conditioned with anti-CD3 mAb but receiving no donor BM or T cell injections also developed clinical signs of GVHD, including weight loss (FIG. 2B).

Since TBI-conditioned recipients have the most severe tissue GVHD in skin and gut 40-50 days after BMT (Zeng 1999; Zeng 2002), four of the chimeric recipients from Example 1 were subjected to histological assessment on day 50 after BMT. Histopathologic specimens were obtained from the skin and small intestine of both the chimeric recipients and control mice treated with anti-CD3 mAb only. Specimens were fixed in formalin, embedded in paraffin blocks, and stained with hematoxylin and eosin using staining procedures described previously (Todorov 1995). Slides were examined at 200× or 400× using an Olympus BX51 fluorescent microscope, equipped with a Pixera cooled CCD camera.

No tissue damage was observed in either tissue in the skin or small intestine of chimeric recipients or control mice treated with anti-CD3 mAb (FIG. 2C). In contrast, TBI-conditioned mice 50 days after BMT showed hyperplasia in the epidermis, lymphocyte infiltration in the dermis, and mucosal atrophy and lymphocyte infiltration in the small intestine (FIG. 2C). These results indicate that, in contrast to TBI conditioning, anti-CD3 mAb conditioning prevents GVHD development.

Example 3

Donor-Specific Tolerance in Chimeric Recipients Generated using Donor BM and Donor CD8+ T Cells Anti-CD3 mAb-conditioned chimeric recipients generated using the method set forth in Example 1 were tested for donor-specific tolerance. The recipients were transplanted with skin grafts from donor FVB/N and non-donor B10A (H-$2^a$) mice 4-8 weeks after BMT. Full-thickness skin grafts ($1 \times 1.5$ cm$^2$) were harvested from the dorsal wall of a donor, placed onto the graft bed on a recipient's left or right back, and covered with Vaseline, gauze, and protective tape. Grafts were inspected on day seven, then daily for the first month, then one time per week thereafter. Grafts were considered rejected at the time of complete sloughing or formation of a dry scab. Time to graft rejection among groups was compared using the log-rank test with a GraphPad Prism Version 3.0 program (Graph Pad Software, San Diego, Calif.).

Figure 3:
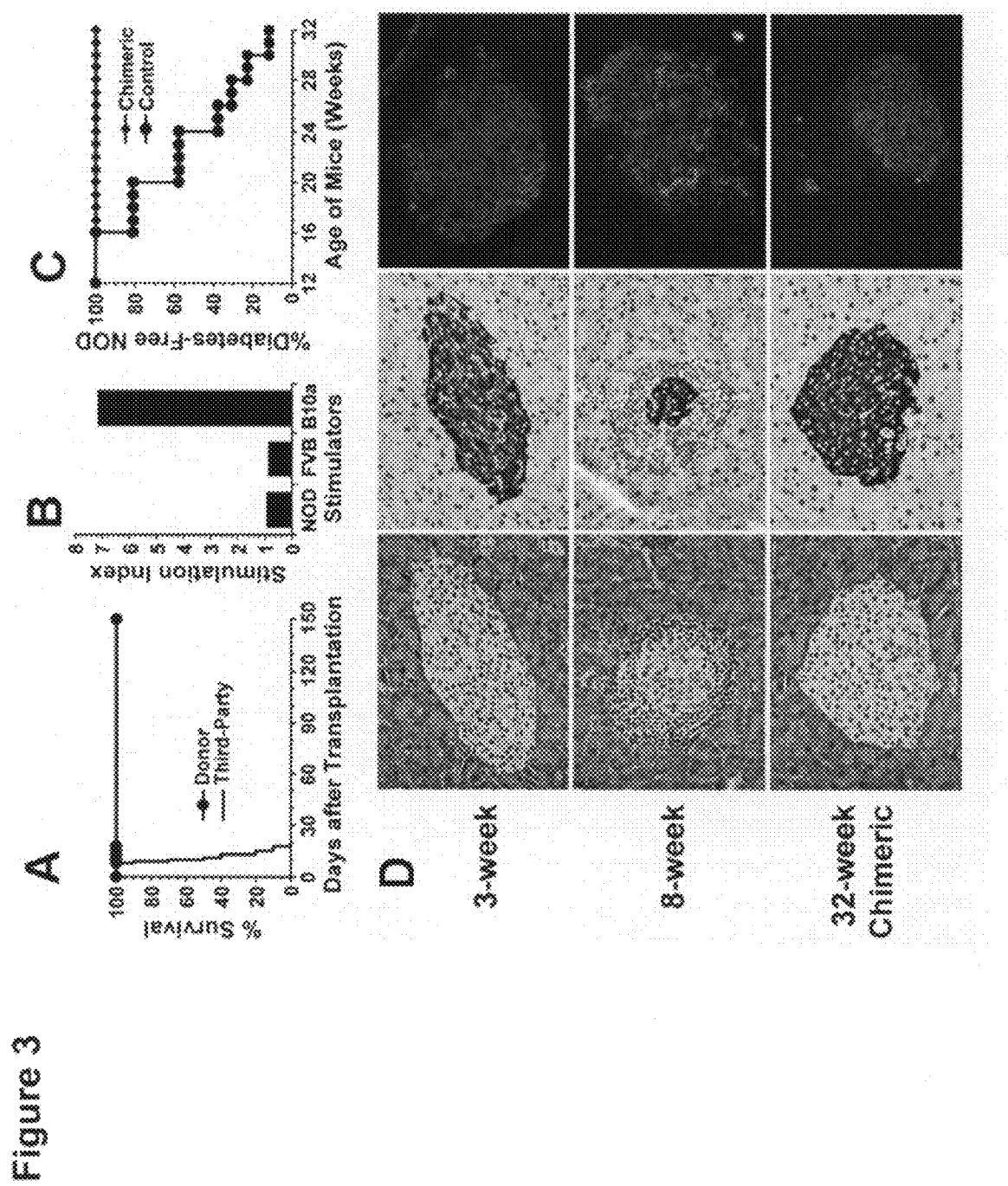
FIG. 3. Donor-specific tolerance and reversal of insulitis in anti-CD3 mAb-conditioned chimeric recipients. A. Chimeric recipients accepted donor skin grafts but rejected third-party non-donor skin grafts. B. Mixed lymphocyte reaction of lymph node cell responders from chimeric recipients at age 32 weeks against donor FVB/N, host NOD, and non-donor B10A spleen cell stimulators. Results are shown for a single representative of three replicate experiments. C. Chimeric recipients (n=12) were resistant to diabetes development as compared to control NOD mice without BMT (n=26). D. Histology of pancreata from 3-week-old NOD mice, 8-week-old NOD mice before anti-CD3 mAb treatment, and 32-week-old chimeric recipients. The tissues from each recipient are shown in HE staining (left column), insulin staining (middle column), and two-color staining of insulin (red) anti-CD3 mAb (green) (right column). Severe lymphocyte infiltration is seen within islets of the 8-week-old NOD mice, but no infiltration was observed in 3-week-old NOD mice before anti-CD3 mAb treatment or 32-week-old chimeric recipients. Results are shown for a single representative of six mice examined.

All of the donor skin grafts survived for more than 150 days, while the non-donor skin grafts were each rejected within 20 days (FIG. 3A, P<0.001). In addition, lymph node cells from the chimeric recipients did not proliferate in response to stimulation by donor or recipient spleen cells, but proliferated vigorously in response to stimulation by non-donor spleen cells (FIG. 3B). These results indicate that donor- or recipient-reactive T cells in the chimeric recipients are deleted or unresponsive.

Figure 4:
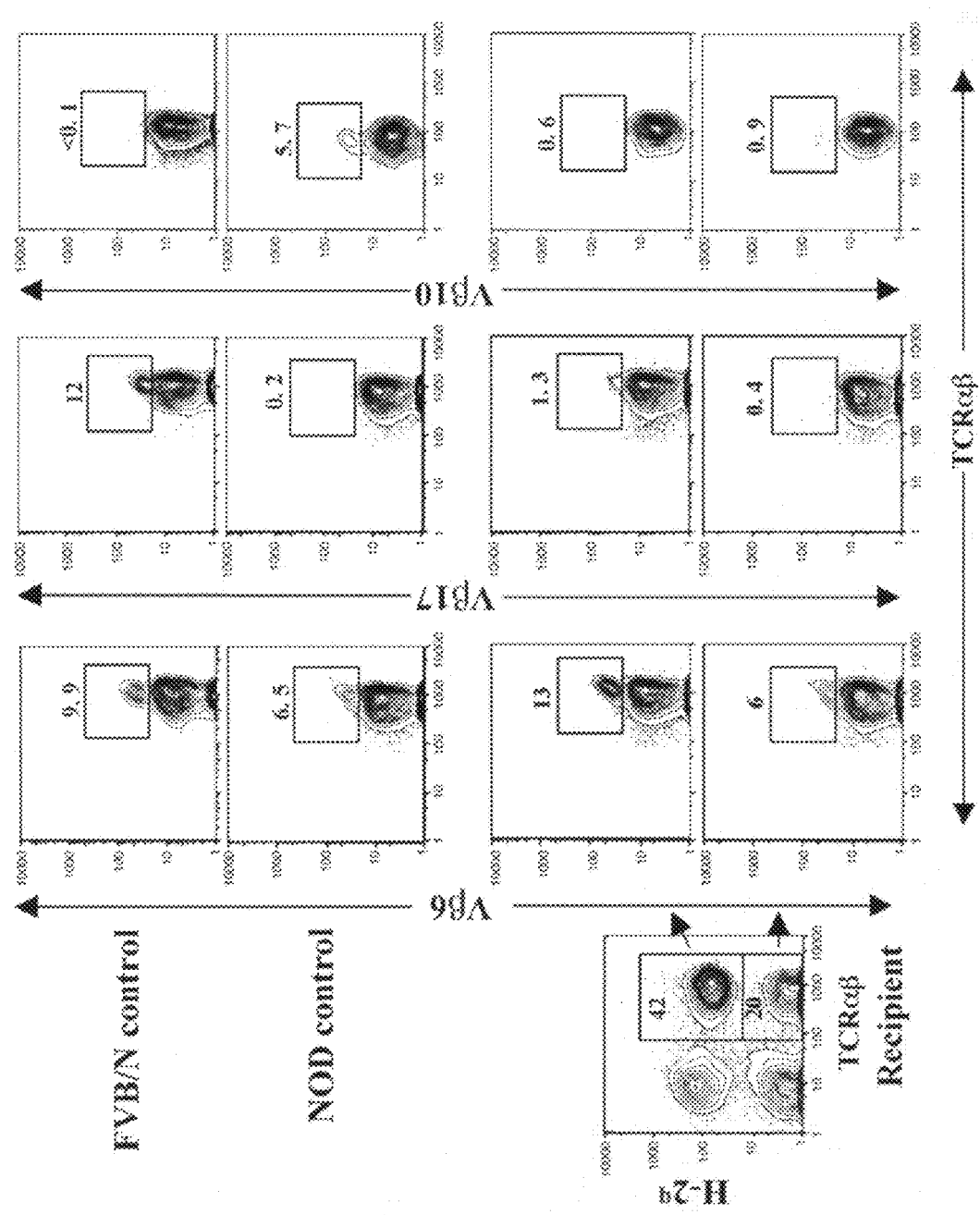
FIG. 4. Clonal deletion of donor- and host-reactive T cells in anti-CD3 mAb-conditioned chimeric recipients. Peripheral blood mononuclear cells (PBMNC) from control FVB/N and NOD mice were stained with anti-TCRαβ versus anti-Vβ6, Vβ17, or Vβ10. The PBMNC from long-term (greater than 24 weeks after BMT) chimeric recipients were stained with anti-H-$2^q$, TCRαβ plus anti-Vβ6, Vβ17 or Vβ10. Donor-type (H-$2^{q+}$) and host-type (H-$2^{q-}$) TCRαβ+ cells were gated, and then shown in TCRαβ versus Vβ6, Vβ17 or Vβ10. The percentage of H-2$^{q+}$ and H-2$^{q-}$ TCRαβ$^+$ cells among PBMNC is shown in the gating boxes. The percentage of Vβ6$^+$, Vβ17$^+$ and Vβ10$^+$ T cell subsets among total T cells is shown above the gating boxes. Results are shown from a single representative of four mice examined.

Clonal deletion is the major mechanism of tolerance induction in chimeric recipients (Sykes 2001; Sykes 2004). Endogenous superantigen-mediated deletion of TCR Vβ subunits has been used previously as an indication of clonal deletion of alloreactive T cells (Wekerle 2000; Beilhack 2003). Superantigen-mediated clonal deletion was measured in the chimeric recipients from Example 1. In control FVB/N donor mice, Vβ6 and Vβ17 were abundant and Vβ10 was deleted (FIG. 4). In control NOD recipient mice, Vβ6 and Vβ10 were abundant and Vβ17 was deleted (FIG. 4). In the chimeric recipients, the FVB/N donor-type T (H-2+TCRαβ+) cells displayed a 10-fold reduction of Vβ17+ cells compared to FVB/N mice (P<0.01), but no reduction of Vβ6+ cells (FIG. 4). This indicates a clonal deletion of Vβ17+ cells mediated by recipient NOD superantigens. In contrast, the NOD host-type T (H-2$^q$TCRαβ+) cells displayed a 5-fold reduction in Vβ10+ cells (P<0.01), but no reduction of Vβ6+ cells (FIG. 4). This indicates a clonal deletion of Vβ10+ cells mediated by donor FVB/N superantigens. This mutual deletion of donor- and host-type T cell subsets in chimeric recipients is consistent with previous reports (Wekerle 2000; Beilhack 2003).

Example 4

Absence of Diabetes Development in Chimeric Recipients Generated Using Donor BM and Donor CD8+ T Cells Anti-CD3 mAb-conditioned chimeric recipients generated using the method set forth in Example 1 were evaluated for development of diabetes. 89% (23/26) of control NOD mice injected only with anti-CD3 mAb developed diabetes (blood glucose>500 mg/dl) by 32 weeks (FIG. 3C, P<0.001). This was similar to the 80% rate of diabetes development in untreated NOD mice (16/20). In contrast, none of the chimeric recipients (0/12) developed diabetes (blood glucose<150 mg/dl) over the 32 week time period (FIG. 3C, P<0.001). It has been reported previously that multiple administrations of anti-CD3 mAb in pre-diabetic NOD mice does not prevent diabetes development, but the same treatment does reverse diabetes in overtly diabetic NOD mice (Chatenoud 1997).

Pancreatic tissue from chimeric recipients and control NOD mice was subjected to immunofluorescence microscopy. Tissue sections were stained with hematoxylin and eosin, insulin, or insulin and anti-CD3 mAb. Double immunofluorescent labeling was performed on 5 μm-thick cryostat sections from snap-frozen pancreatic tissues. Insulin staining was performed using a Tech-mate 1000 autostainer (Ventana, Tucson, Ariz.). Stained sections were visualized by immunofluorescent microscopy at 200× or 400× magnification, using an Olympus BX51 fluorescent microscope equipped with a Pixera cooled CCD camera. Fluorescent images relative to each marker were collected using a corresponding filter set. Color composite images were generated using Adobe Photoshop 7.0 software (Adobe Systems, San Jose, Calif.).

The chimeric recipients displayed no reduction in insulin staining after 32 weeks (FIG. 3D). In addition, the chimeric recipients all (6/6) displayed a lack of lymphocyte infiltration in their islets (FIG. 3D). In contrast, all of the untreated NOD control mice (6/6) showed severe lymphocyte infiltration. These results indicate that mixed chimerism in prediabetic NOD mice reverses insulitis and prevents the development of diabetes.

Example 5

Figure 5:
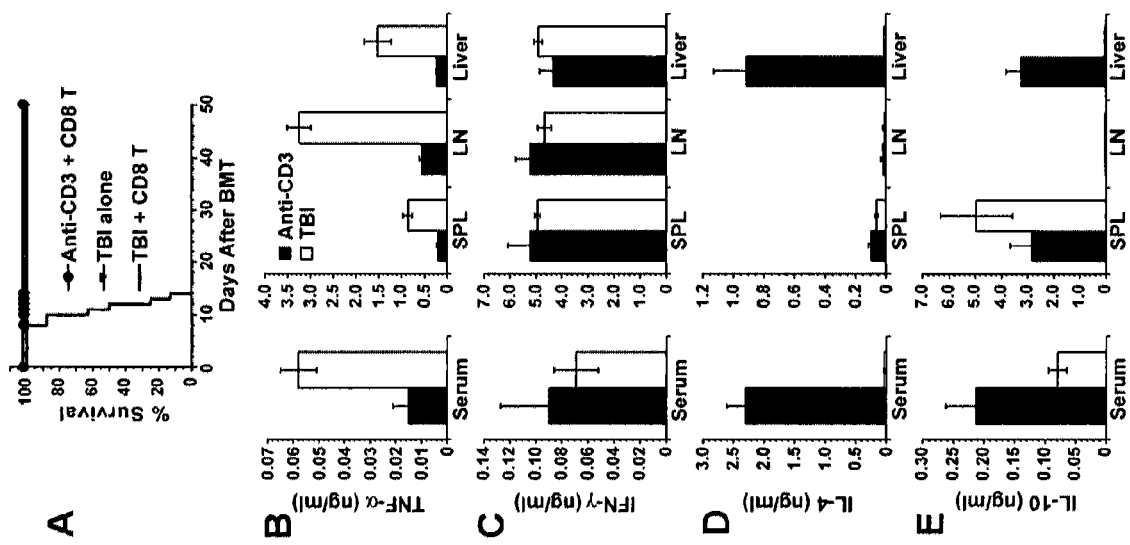
FIG. 5. Cytokine secretion profiles of anti-CD3 mAb- vs. TBI-conditioned chimeric recipients. A. Survival of chimeric recipients conditioned with anti-CD3 mAb or TBI after injection of donor TCD-BM (2×10$^6$) and CD8$^+$ T cells (20×10$^6$). There were eight mice in each group. B.-E. TNF-α, IFN-γ, IL4, and IL-10 in serum and culture supernatant of chimeric recipients from the two groups. Values are the mean±SE of individual recipients in each group (n=8).

Cytokine Profile Comparison between TBI- and Anti-CD3 mAb-Conditioned Chimeric Recipients Inflammatory cytokines such as TNF-α play a critical role in the induction of GVHD in TBI-conditioned recipients (Ferrara 2000; Teshima 2002). Other cytokines, such as IL-4 and IL-10 secreted by T and dendritic cells, suppress GVHD (Zeng 1999; Lan 2001; Zeng 2002; Cooke 2003; Zeng 2004). Cytokine profiles were obtained for sixteen chimeric recipients injected with $2\times10^6$ donor BM cells and $20\times10^6$ donor spleen $CD8^+$ T cells from FVB/N donors. Eight of the sixteen recipients had been conditioned with TBI, while the other eight had been conditioned with anti-CD3 mAb. In order to avoid the influence of T cells in donor BM, the BM cells were T cell depleted (TCD). All eight TBI-conditioned chimeric recipients developed severe clinical signs of GVHD and died within two weeks after BMT (FIG. 5A). In contrast, all eight anti-CD3-conditioned chimeric recipients showed no signs of GVHD, and all survived for more than 50 days after BMT (FIG. 5A). Control mice given TBI conditioning alone also survived for more than 50 days (FIG. 5A).

Cytokine profiles were obtained for each of the sixteen chimeric recipients from both serum and culture supernatants. Sera were harvested at 0, 3, and 5 days after BMT. Culture supernatants were from a 48-hour culture of $0.5\times10^6$ mononuclear cells from the spleen, lymph node, or liver. Culture cells were stimulated with plate-bound anti-CD3 mAb (145-2C11) and 5 µg/ml soluble anti-CD28 (37.51, BD Pharmingen, San Diego, Calif.). Cytokines were measured using the Luminex Lab MAP system and ELISA kits (Biosource International, Camarillo, Calif.) as described previously (Zeng 2002; Goudy 2003).

Serum cytokine levels were undetectable on day 0 and peaked on day 5. Anti-CD3 mAb-conditioned chimeric recipients had 4-fold lower levels of serum TNF-α than TBI-conditioned recipients (FIG. 5B, $P<0.01$), but 50-fold higher IL-4 levels and 3-fold higher IL-10 levels (FIG. 5D and 5E, $P<0.01$). Mononuclear cells from the spleen, lymph node, and liver of the anti-CD3-conditioned chimeric recipients secreted 5-10 fold lower levels of TNF-α than TBI-conditioned recipients at 5 days after BMT (FIG. 5B, $P<0.01$). Liver mononuclear cells from the anti-CD3-conditioned chimeric recipients secreted more than 20-fold higher levels of IL-4 and IL-10 than TBI-conditioned recipients at 5 days after BMT (FIGS. 5D and 5E, $P<0.01$). The IFN-γ levels in sera and culture supernatants was similar for all sixteen recipients (FIG. 5C, $P>0.1$). These results establish that following donor $CD8^+$ T cell injection, anti-CD3-conditioned chimeric recipients secrete lower levels of pro-inflammatory TNF-α and higher levels of anti-inflammatory IL-4 and IL-10 than recipients conditioned with TBI.

Figure 6:
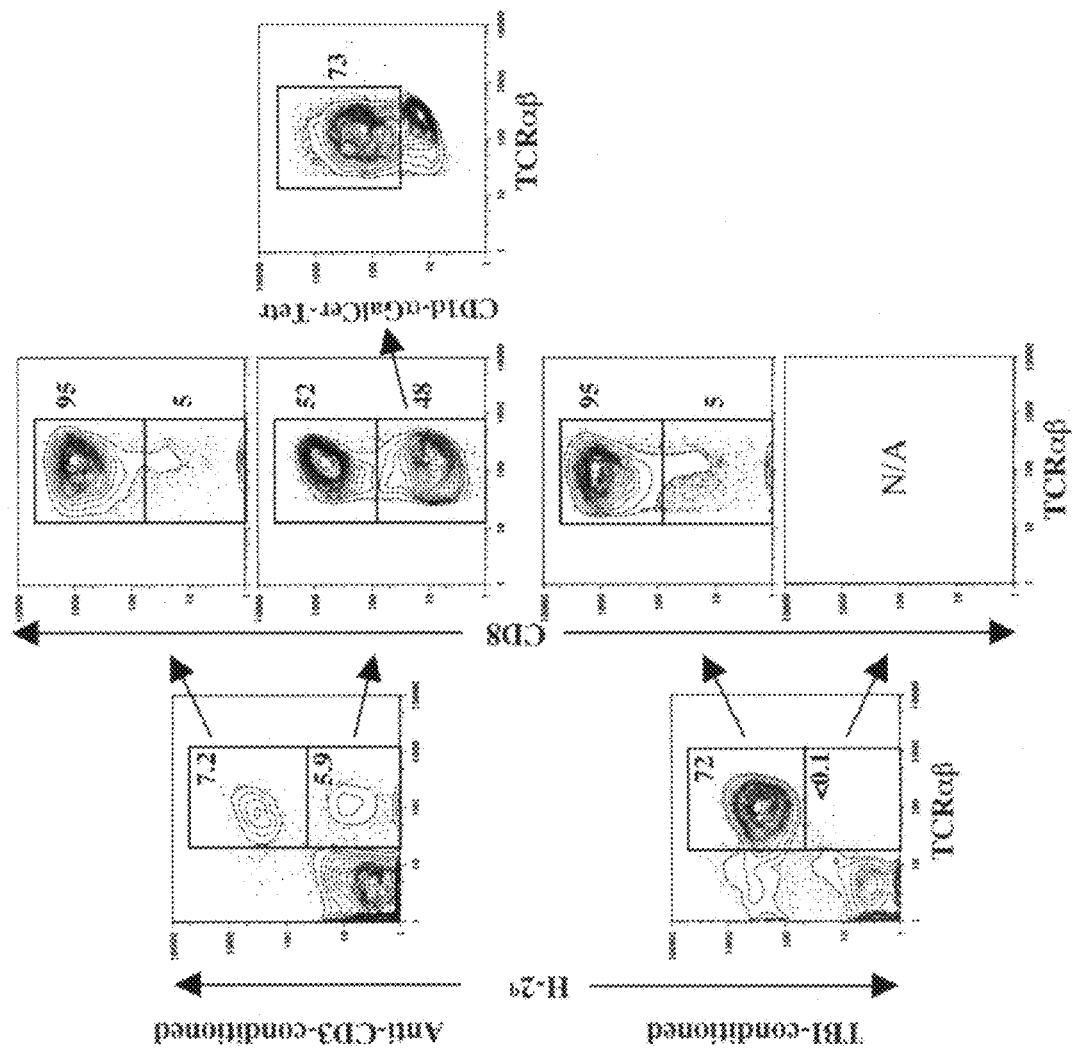
FIG. 6. NKT cell levels among liver mononuclear cells of anti-CD3 mAb-conditioned recipients. Mononuclear cells from the livers of anti-CD3 mAb- or TBI-conditioned chimeric recipients five days after BMT were stained with anti-H-2$^q$, anti-TCαβ, anti-CD8, and CD1d-αGalCer-tetramer. The TCRαβ$^+$ cells were first gated into H-2$^{q+}$ and H-2$^{q-}$, then both were shown in TCRαβ versus CD8. The gated TCRαβH-2$^{q-}$ CD8$^-$ cells were further shown in TCRαβ versus CD1d-αGalCer-tetramer. The percentage of each gated population among total cells is shown inside or beside the gating boxes. Results are shown for a single representative of four mice examined.

To identify the source of IL-4 and IL-10 production in liver mononuclear cells from the anti-CD3-conditioned chimeric recipients, liver mononuclear cells from all sixteen samples were analyzed to determine which percentage were natural killer T (NKT) cells. It is well known that the percentage of NKT cells among liver T cells is normally high, and that NKT cells secrete large amounts of IL-4 and IL-10 upon primary stimulation (Kronenberg 2002; Taniguchi 2003). All TCRαβ$^+$ cells among the liver mononuclear cells from the TBI-conditioned recipients were donor-type, and 95% were donor $CD8^+$ T cells (FIG. 6). In contrast, there were both donor- and host-type T cells among the liver mononuclear cells from the anti-CD3 mAb-conditioned recipients, and the percentage and yield of donor T cells was 10-fold lower than that of the TBI-conditioned recipients ($P<0.01$, FIG. 6). These results are summarized in Table 2, below.

TABLE 2

| Conditioning | Tissue | Yield of mononuclear cells ($\times10^6$) | % donor-type $CD8^+$ T cells | Yield of donor-type $CD8^+$ T cells ($\times10^6$) |
|---|---|---|---|---|
| Anti-CD3 mAb | Liver | 3.2 ± 0.5 | 5.6 ± 1.1 | 0.17 ± 0.08 |
| | Spleen | 282 ± 23 | 4.7 ± 1.5 | 14.5 ± 1.2 |
| | Lymph node | 3.6 ± 0.7 | 7.5 ± 2.2 | 0.31 ± 0.11 |
| TBI | Liver | 2.1 ± 0.8 | 76 ± 4.5 | 1.86 ± 0.12 |
| | Spleen | 12 ± 3.2 | 61 ± 8.9 | 8.3 ± 0.7 |
| | Lymph Node | 0.4 ± 0.1 | 71 ± 5.4 | 0.28 ± 0.17 |

There were both $CD4^+$ and $CD8^+$ T cells among the residual host T cells from the anti-CD3 mAb-conditioned recipients. Approximately 73% of the host $CD8^-$ (including $CD4^+$ and $CD4^-CD8^-$) T cells were CD1d-αGalCer-tetramer$^+$ T cells, while both donor and host $CD8^+$ T cells were all CD1d-αGalCer-tetramer$^-$. Without wishing to be bound by an theory, these results suggest that host-type NKT cells in the liver of the anti-CD3 mAb-conditioned recipients may be the major source of IL-4 and IL-10 production early after BMT.

Example 6

Donor CD8+ T Cells in Anti-CD3 mAb-Conditioned Chimeric Recipients Expand in Host Lymphohematopoietic Tissues Anti-CD3 mAb-conditioned chimeric recipients given donor $CD8^+$ T and BM cells did not display lymphocyte infiltration in their skin or intestinal tissues, but TBI-conditioned recipients given the same dose of donor $CD8^+$ T and BM cells showed heavy lymphocyte infiltration in both those tissues (FIG. 2C). Expansion of donor $CD8^+$ T cells was measured in the spleen, lymph nodes, and liver of the two kinds of recipients was measured as well. Five days after BMT, anti-CD3 mAb-conditioned chimeric recipients given $20\times10^6$ $CD8^+$ T cells in combination with $2\times10^6$ TCD-BM cells showed much larger spleens than TBI-conditioned chimeric recipients given the same dose of donor $CD8^+$ T and BM cells. In addition, the livers of the anti-CD3 mAb-conditioned recipients looked normal, while the liver of the TBI-conditioned recipients looked pale and decayed. Histopathology studies showed little lymphocyte infiltration in the anti-CD3 mAb-conditioned recipient liver tissue, but massive lymphocyte infiltration in the TBI-conditioned liver tissue. Flow cytometric analysis showed that all TCRαβ$^+$ T cells in the spleen, lymph node, and liver of TBI-conditioned recipients were donor-type, while TCRαβ$^+$ T cells in the same tissues of anti-CD3 mAb-conditioned recipients contained both donor- and host-type (FIG. 6). The percentage of donor-type T cells in these tissues in TBI-conditioned recipients was 10-fold higher than in anti-CD mAb-conditioned recipients (FIG. 6; Table 2).

The yield of donor CD8+ T cells in the spleen, lymph node, and liver of both types of recipients was determined. Previous studies showed that five days after BMT, all donor-type T cells in the tissues of recipients were injected donor T cells (Zeng 2002). As seen in Table 2, the yield of donor CD8+ T cells in the spleen of anti-CD3 mAb-conditioned recipients was significantly higher than that of TBI-conditioned recipients (P<0.05), due to an increase of about 20-fold in spleen mononuclear cells as compared to TBI-conditioned recipients. In contrast, the yield of CD8+ T cells from the liver of anti-CD3 mAb-conditioned recipients was 10-fold less than that of TBI-conditioned recipients (P<0.01), due to a 10-fold lower percentage of donor CD8+ T cells in the anti-CD3 mAb-conditioned recipients than in the TBI-conditioned recipients. The yield of donor CD8+ T cells in the lymph nodes was similar in both types of recipients. These results suggest that donor CD8+ T cells expand predominantly in lymphohematopoietic tissues such as spleen and lymph node in recipients conditioned with anti-CD3 mAb, while they expand in both lymphohematopoietic tissues and GVHD target tissues such as liver, gut, and skin in recipients conditioned with TBI.

As stated above, the foregoing are merely intended to illustrate the various embodiments of the present invention. As such, the specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Annunziato, F., et al. 1999. Assessment of chemokine receptor expression by human Th1 and Th2 cells in vitro and in vivo. J Leukoc Biol 65:691-699.
2. Atkinson, M. A., Leiter, E. H. 1999. The NOD mouse model of type 1 diabetes: as good as it gets? Nat Med 5:601-604.
3. Beilhack, G. F., et al. 2003. Purified allogeneic hematopoietic stem cell transplantation blocks diabetes pathogenesis in NOD mice. Diabetes 52:59-68.
4. Belghith, M., et al. 2003. TGF-beta-dependent mechanisms mediate restoration of self-tolerance induced by antibodies to CD3 in overt autoimmune diabetes. Nat Med 9:1202-1208.
5. Blazar, B. R., Taylor, P. A., Vallera, D. A. 1994. In vivo or in vitro anti-CD3 epsilon chain monoclonal antibody therapy for the prevention of lethal murine graft-versus-host disease across the major histocompatibility barrier in mice. J Immunol 152:3665-3674.
6. Blazar, B. R., et al. 1997. Anti-CD3 epsilon F(ab')2 fragments inhibit T cell expansion in vivo during graft-versus-host disease or the primary immune response to nominal antigen. J Immunol 159:5821-5833.
7. Bluestone, J. A., Abbas, A. K. 2003. Natural versus adaptive regulatory T cells. Nat Rev Immunol 3:253-257.
8. Burt, R. K., Traynor, A. 1998. Hematopoietic stem cell therapy of autoimmune diseases. Curr Opin Hematol 5:472-477.
9. Campbell, D. J., et al. 2003. Targeting T cell responses by selective chemokine receptor expression. Semin Immunol 15:277-286.
10. Castano, L., Eisenbarth, G. S. 1990. Type-I diabetes: a chronic autoimmune disease of human, mouse, and rat. Annu Rev Immunol 8:647-679.
11. Chatenoud, L., Primo, J., Bach, J. F. 1997. CD3 antibody-induced dominant self tolerance in overtly diabetic NOD mice. J Immunol 158:2947-2954.
12. Cooke, K. R., Ferrara, J. L. 2003. A protective gene for graft-versus-host disease. N Engl J Med 349:2183-2184.
13. Dor, Y., Brown, J., Martinez, O., Melton, D. A. 2004. Adult pancreatic beta-cells are formed by self-duplication rather than stem-cell differentiation. Nature 429:41-46.
14. Exner, B. G., Groninger, J. H., Ildstad, S. T. 1997. Bone marrow transplantation for therapy in autoimmune disease. Stem Cells 15(suppl 1):171-175.
15. Ferrara, J. L. 2000. Pathogenesis of acute graft-versus-host disease: cytokines and cellular effectors. J Hematother Stem Cell Res 9:299-306.
16. Ferrara, J., Antin, J. 2004. The pathophysiology of Graft-vs-Host Disease. Hematopoietic Cell Transplantation. Malden: Blackwell Science Ltd. 353-368.
17. Gandy, K. L., Domen, J., Aguila, H., Weissman, I. L. 1999. CD8+TCR+ and CD8+TCR-cells in whole bone marrow facilitate the engraftment of hematopoietic stem cells across allogeneic barriers. Immunity 11:579-590.
18. Gonzalez, M., et al. 2002. The balance between donor T cell anergy and suppression versus lethal graft-versus-host disease is determined by host conditioning. J Immunol 169:5581-5589.
19. Goudy, K. S., et al. 2003. Systemic overexpression of IL-10 induces CD4+CD25+ cell populations in vivo and ameliorates type 1 diabetes in nonobese diabetic mice in a dose-dependent fashion. J Immunol 171:2270-2278.
20. Hancock, W. W., et al. 2000. Requirement of the chemokine receptor CXCR3 for acute allograft rejection. J Exp Med 192:1515-1520.
21. Hancock, W. W., et al. 2001. Donor-derived IP-10 initiates development of acute allograft rejection. J Exp Med 193:975-980.
22. Herold, K. C., et al. 2002. Anti-CD3 monoclonal antibody in new-onset type 1 diabetes mellitus. N Engl J Med 346:1692-1698.
23. Hill, G. R., et al. 1997. Total body irradiation and acute graft-versus-host disease: the role of gastrointestinal damage and inflammatory cytokines. Blood 90:3204-3213.
24. Ianus, A., Holz, G. G., Theise, N. D., Hussain, M. A. 2003. In vivo derivation of glucose-competent pancreatic endocrine cells from bone marrow without evidence of cell fusion. J Clin Invest 111:843-850.
25. Kaufman, C. L., Li, H., Ildstad, S. T. 1997. Patterns of hemopoietic reconstitution in nonobese diabetic mice: dichotomy of allogeneic resistance versus competitive advantage of disease-resistant marrow. J Immunol 158:2435-2442.
26. Kim, Y. M., et al. 2003. Graft-versus-host disease can be separated from graft-versus-lymphoma effects by control of lymphocyte trafficking with FTY720. J Clin Invest 111:659-669.
27. Kim, Y. M., et al. 2004. Graft-versus-host-reactive donor CD4 cells can induce T cell-mediated rejection of the donor marrow in mixed allogeneic chimeras prepared with nonmyeloablative conditioning. Blood 103:732-739.
28. Kodama, S., et al. 2003. Islet regeneration during the reversal of autoimmune diabetes in NOD mice. Science 302:1223-1227.
29. Kronenberg, M., Gapin, L. 2002. The unconventional lifestyle of NKT cells. Nat Rev Immunol 2:557-568.

30. Kunkel, E. J., et al. 2000. Lymphocyte CC chemokine receptor 9 and epithelial thymus-expressed chemokine (TECK) expression distinguish the small intestinal immune compartment: Epithelial expression of tissue-specific chemokines as an organizing principle in regional immunity. J Exp Med 192:761-768.

31. Lan, F., et al. 2001. Predominance of NK1.1$^+$TCR alpha beta$^+$ or DX5$^+$TCR alpha beta$^+$ T cells in mice conditioned with fractionated lymphoid irradiation protects against graft-versus-host disease: "natural suppressor" cells. J Immunol 167:2087-2096.

32. Li, H., et al. 1996. Mixed allogeneic chimerism induced by a sublethal approach prevents autoimmune diabetes and reverses insulitis in nonobese diabetic (NOD) mice. J Immunol 56:380-388.

33. Loetscher, P., et al. 1998. CCR5 is characteristic of Th1 lymphocytes. Nature 391:344-345.

34. Martin, P. J. 1993. Donor CD8 cells prevent allogeneic marrow graft rejection in mice: potential implications for marrow transplantation in humans. J Exp Med 178:703-712.

35. Martin, P. J., et al. 1999. A phase I-II clinical trial to evaluate removal of CD4 cells and partial depletion of CD8 cells from donor marrow for HLA-mismatched unrelated recipients. Blood 94:2192-2199.

36. Murai, M., et al. 1999. Active participation of CCR5$^+$ CD8$^+$ T lymphocytes in the pathogenesis of liver injury in graft-versus-host disease. J Clin Invest 104:49-57.

37. Nakajima, C., et al. 2002. Induction of the chemokine receptor CXCR3 on TCR-stimulated T cells: dependence on the release from persistent TCR-triggering and requirement for IFN-gamma stimulation. Eur J Immunol 32:1792-1801.

38. Nikolic, B., et al. 2004. Mixed hematopoietic chimerism allows cure of autoimmune diabetes through allogeneic tolerance and reversal of autoimmunity. Diabetes 53:376-383.

39. Olson, T. S., Ley, K. 2002. Chemokines and chemokine receptors in leukocyte trafficking. Am J Physiol Regul Integr Comp Physiol 283:R7-28.

40. Patterson, B. K., et al. 1999. Regulation of CCR5 and CXCR4 expression by type 1 and type 2 cytokines: CCR5 expression is downregulated by IL-10 in CD4-positive lymphocytes. Clin Immunol 91:254-262.

41. Pelot, M. R., et al. 1999. Lymphohematopoietic graft-vs.-host reactions can be induced without graft-vs.-host disease in murine mixed chimeras established with a cyclophosphamide-based nonmyeloablative conditioning regimen. Biol Blood Marrow Transplant 5:133-143.

42. Picker, L. J., Michie, S. A., Rott, L. S., Butcher, E. C. 1990. A unique phenotype of skin-associated lymphocytes in humans. Preferential expression of the HECA-452 epitope by benign and malignant T cells at cutaneous sites. Am J Pathol 136:1053-1068.

43. Ricordi, C. 2003. Islet transplantation: a brave new world. Diabetes 52:1595-1603.

44. Rossini, A. A. 2004. Autoimmune diabetes and the circle of tolerance. Diabetes 53:267-275.

45. Seung, E., et al. 2000. Allogeneic hematopoietic chimerism in mice treated with sublethal myeloablation and anti-CD154 antibody: absence of graft-versus-host disease, induction of skin allograft tolerance, and prevention of recurrent autoimmunity in islet-allografted NOD/Lt mice. Blood 95:2175-2182.

46. Seung, E., Mordes, J. P., Rossini, A. A., Greiner, D. L. 2003. Hematopoietic chimerism and central tolerance created by peripheral-tolerance induction without myeloablative conditioning. J Clin Invest 112:795-808.

47. Shlomchik, W. D., et al. 1999. Prevention of graft versus host disease by inactivation of host antigen-presenting cells. Science 285:412-415.

48. Soiffer, R. J. 2004. T-cell depletion to prevent Graft-vs-Host Disease. Hematopoietic cell transplantation. Malden: Blackwell Science Ltd. 221-233.

49. Sullivan, K. M., Furst, D. E. 1997. The evolving role of blood and marrow transplantation for the treatment of autoimmune diseases. J Rheumatol Suppl 48:1-4.

50. Sullivan, K. M. 2004. Graft-vs-host desease. Hematopoietic cell transplantation. Malden: Blackwell Science Ltd. 635.

51. Sykes, M., Sheard, M. A., Sachs, D. H. 1988. Graft-versus-host-related immunosuppression is induced in mixed chimeras by alloresponses against either host or donor lymphohematopoietic cells. J Exp Med 168:2391-2396.

52. Sykes, M. 2001. Mixed chimerism and transplant tolerance. Immunity 14:417-424.

53. Sykes, M. 2004. Mechanisms of Tolerance. Hematopoietic Cell Transplantation. Madden: Blackwell Science Ltd.

54. Taniguchi, M., et al. 2003. The regulatory role of Valpha14 NKT cells in innate and acquired immune response. Annu Rev Immunol 21:483-513.

55. Teshima, T., et al. 2002. Acute graft-versus-host disease does not require alloantigen expression on host epithelium. Nat Med 8:575-581.

56. Todorov, I. T., Attaran, A., Kearsey, S. E. 1995. BM28, a human member of the MCM2-3-5 family, is displaced from chromatin during DNA replication. J Cell Biol 129:1433-1445.

57. Wagner, J. L., et al. 1998. The development of chronic graft-versus-host disease: an analysis of screening studies and the impact of corticosteroid use at 100 days after transplantation. Bone Marrow Transplant 22:139-146.

58. Wekerle, T., et al. 2000. Allogeneic bone marrow transplantation with co-stimulatory blockade induces macrochimerism and tolerance without cytoreductive host treatment. Nat Med 6:464-469.

59. Zeng, D., et al 1999. Bone marrow NK1.1(−) and NK1.1 (+) T cells reciprocally regulate acute graft versus host disease. J Exp Med 189:1073-1081.

60. Zeng, D., et al. 2000. Cutting edge: a role for CD1 in the pathogenesis of lupus in NZB/NZW mice. J Immunol 164:5000-5004.

61. Zeng, D., et al. 2002. Unique patterns of surface receptors, cytokine secretion, and immune functions distinguish T cells in the bone marrow from those in the periphery: impact on allogeneic bone marrow transplantation. Blood 99:1449-1457.

62. Zeng, D., et al. 2003a. Different patterns of migration and expansion of blood and marrow CD4 T cells in lymphoid and non-lymphoid tissues result in a different capacity to induce Graft-vs-Host Disease. The American Association of Immunologists 90th Anniversary Annual Meeting. Denver, Colo.: FASEB C59.

63. Zeng, D., et al. 2003b. Activation of natural killer T cells in NZB/W mice induces Th1-type immune responses exacerbating lupus. J Clin Invest 112:1211-1222.

64. Zeng, D., Lan, F., Hoffmann, P., Strober, S. 2004. Suppression of graft-versus-host disease by naturally occurring regulatory T cells. Transplantation 77:S9-S11.

What is claimed is:

1. A method of generating chimerism in a recipient, wherein the method comprises:
   a) administering a therapeutically effective amount of anti-CD3 mAb directly to a bone marrow transplantation site in said recipient;
   b) administering a therapeutically effective amount of donor bone marrow cells and donor CD8$^+$ T cells to said recipient five to ten days after step (a); and
   c) repeating step (b) 14 days after step (a).

2. The method of claim 1 wherein step (b) is carried out seven days after step (a).

* * * * *

UNITED STATES PATENT AND TRADEMARK OFFICE
CERTIFICATE OF CORRECTION

| | | |
|---|---|---|
| PATENT NO. | : 8,277,811 B2 | Page 1 of 1 |
| APPLICATION NO. | : 11/699641 | |
| DATED | : October 2, 2012 | |
| INVENTOR(S) | : Zeng | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 644 days.

Signed and Sealed this
Twenty-sixth Day of August, 2014

Michelle K. Lee
*Deputy Director of the United States Patent and Trademark Office*